US007294506B2

(12) United States Patent
Daniell et al.

(10) Patent No.: US 7,294,506 B2
(45) Date of Patent: Nov. 13, 2007

(54) TOBACCO CHLOROPLAST TRANSFORMATION VECTORS COMPRISING A MULTI-GENE OPERON ENCODING A BIOPHARMACEUTICAL PROTEIN AND A CHAPERONIN

(75) Inventors: Henry Daniell, Winter Park, FL (US); William Moar, Auburn University, AL (US)

(73) Assignee: University Central Florida Research Foundation, Inc.

( * ) Notice: Subject to any disclaimer, the term of this patent is extended or adjusted under 35 U.S.C. 154(b) by 33 days.

(21) Appl. No.: 10/770,183

(22) Filed: Feb. 2, 2004

(65) Prior Publication Data

US 2004/0210966 A1 Oct. 21, 2004

Related U.S. Application Data

(63) Continuation of application No. 09/807,723, filed as application No. PCT/US01/06276 on Feb. 28, 2001, now abandoned.

(60) Provisional application No. 60/266,121, filed on Feb. 2, 2001, provisional application No. 60/259,248, filed on Dec. 29, 2000, provisional application No. 60/257,408, filed on Dec. 22, 2000, provisional application No. 60/185,660, filed on Feb. 29, 2000.

(51) Int. Cl.
C12N 15/82 (2006.01)
(52) U.S. Cl. .................................................. 435/320.1
(58) Field of Classification Search ...................... None
See application file for complete search history.

(56) References Cited

U.S. PATENT DOCUMENTS

| 5,250,515 | A | 10/1993 | Fuchs et al. |
| 5,436,392 | A | 7/1995 | Thomas et al. |
| 5,545,817 | A | 8/1996 | McBride et al. |
| 5,545,818 | A | 8/1996 | McBride et al. |
| 5,571,722 | A | 11/1996 | Rosson |
| 5,661,017 | A | 8/1997 | Dunahay et al. |
| 5,693,507 | A | 12/1997 | Daniell et al. |
| 5,763,245 | A | 6/1998 | Greenplate |
| 5,766,885 | A | 6/1998 | Carrington et al. |
| 5,869,719 | A | 2/1999 | Patton |
| 5,877,402 | A * | 3/1999 | Maliga et al. ............... 800/298 |
| 5,932,479 | A | 8/1999 | Daniell et al. |
| 5,958,745 | A | 9/1999 | Gruys et al. |
| 5,965,796 | A | 10/1999 | Meagher et al. |
| 6,004,782 | A | 12/1999 | Daniell et al. |
| 6,140,486 | A | 10/2000 | Facciotti et al. |

FOREIGN PATENT DOCUMENTS

| WO | WO99/05265 | * | 2/1999 |
| WO | WO99/10513 | * | 3/1999 |
| WO | WO99/66026 A2 | | 12/1999 |
| WO | WO 00/03012 | | 1/2000 |
| WO | WO 01/07590 A2 | | 2/2001 |

OTHER PUBLICATIONS

Baumann, L. et al. "Sequence Analysis of the Mosquitocidal Toxin Genes Encoding 51.4- and 41.9-Kilodalton Proteins from *Bacillus sphaericus* 2362 and 2297," *Journal of Bacteriology*, May 1988, pp. 2045-2050, vol. 170, No. 5.
Begley, T.P. et al. "Mechanistic Studies of a Protonolytic Organomercurial Cleaving Enzyme: Bacterial Organomercurial Lyase," *Biochemistry*, 1986, pp. 7192-7200, vol. 25.
Bernier, M. et al. "Mercury Inhibition At The Donor Side Of Photosystem II Is Reversed By Chloride," *FEBS*, Apr. 1993, pp. 19-23, vol. 321, No. 1.
Bizily, S.P. et al. Phytoremediation Of Methylmercury Pollution: *Merb* Expression in *Arabidopsis thaliana* Confers Resistance To Organomercurials, *Proc. Natl. Acad. Sci. USA*, Jun. 1999, pp. 6808-6813, vol. 96.
Boston, R.S. et al. "Molecular Chaperones And Protein Folding In Plants," *Plant Molecular Biology*, 1996, pp. 191-222, vol. 32.
Bradley, D. et al. "The Insecticidal CrylB Crystal Protein of *Bacillus thuringiensis* ssp. *Thuringiensis* Has Dual Specificity to Coleopteran and Lepidopteran Larvae," *Journal of Invertebrate Pathology*, 1995, pp. 162-173, vol. 65.
Carlson, P. "The Use Of Protoplasts For Genetic Research," *PNAS*, USA Feb. 1973, pp. 598-602, vol. 70, No. 2.
Clewell, D.B. et al. "Conjugative Transposons And The Dissemination Of Antibiotic Resistance In *Streptococci*," *Ann. Rev. Microbiol.*, 1986, pp. 635-659, vol. 40.
Crickmore, N. et al. "Revision of the Nomenclature for the *Bacillus thuringiensis* Pesticidal Crystal Proteins," *Microbiology and Molecular Biology Reviews*, Sep. 1998, pp. 807-813, vol. 62, No. 3.
Daniell, H. "GM Crops: Public Perception And Scientific Solutions," *Trends in Plant Science* Dec. 1999, pp. 467-469, vol. 4, No. 12.
Daniell, H. et al. "Engineering Plants For Stress Tolerance Via Organelle Genomes," *NATO ASI Series*, 1994, pp. 589-604, vol. H86.
Daniell, H. et al. "In Vitro Synthesis Of Photosynthestic Membranes: Development Of Photosystem I Activity And Cyclic Photophosphorylation," *Biochem. Biophys. Res. Comm.*, Mar. 16, 1983, pp. 740-749, vol. 111, No. 2.
Daniell, H. et al. "Milestones in Chloroplast Genetic Engineering: An Environmentally Friendly Era in Biotechnology," *TRENDS in Plant Science*, Feb. 2003, pp. 84-91, vol. 7, No. 2.
Daniell, H. et al. "Oxygenetic Photoreduction Of Methyl Viologen And Nicotinamide Adfnine Dinucleotide Phosphate Without The Involvement Of Photosystem I During Plastid Development," *Biochem. Biophys. Res. Comm.*, Feb. 15, 1985, pp. 1114-1121, vol. 126, No. 3.

(Continued)

*Primary Examiner*—Anne Kubelik
(74) *Attorney, Agent, or Firm*—Saliwanchik, Lloyd & Saliwanchik

(57) ABSTRACT

The subject invention relates in part to tobacco chloroplast transformation vectors comprising a multi-gene operon that generates a polycistron that encodes a biopharmaceutical protein and a chaperonin.

2 Claims, 18 Drawing Sheets

OTHER PUBLICATIONS

Daniell, H. "Transformation and Foreign Gene Expression in Plants Mediated by Microprojectile Bombardment," *Methods in Molecular Biology*, pp. 463-489, vol. 62: Recombinant Gene Expression Protocols.

Daniell, H. et al. "Transformation of the Cynobacterium *Anacystis nidulans* 6301 with the *Escherichia coli* Plasmid pBR322," *PNAS, USA*, Apr. 1986, pp. 2546-2550, vol. 83.

Daniell, H. et al. "Transient Foreign Gene Expression In Chloroplasts Of Cultured Tobacco Cells After Biolistic Delivery Of Chloroplast Vectors," *Proc. Natl. Acad. Sci. USA*, Jan. 1990, pp. 88-92, vol. 87.

Daniell, H. et al. "Uptake And Expression Of Bacterial And Cyanobacterial Genes By Isolated Cucumber Etioplasts," *PNAS*, Sep. 1987, pp. 6349-6353, vol. 84.

De Cosa, B. et al. "Overexpression of the *Bt cry2Aa2* Operon In Chloroplasts Leads To Formation Of Insecticidal Crystals," *Nature Biotechnology*, Jan. 2001, pp. 71-74, vol. 19.

De Wilde, C. et al. "Plants As Bioreactors For Protein Production: Avoiding The Problem Of Transgene Silencing," *Plant Molecular Biology*, 2000, pp. 347-359, vol. 43.

Dhingra, A. et al. "Expression of glpA/B Operon in Transgenic Chloroplasts to Degrade Glyphosate," In vitro *Animal: Abstracts for posters presented at the 10th IAPTC&B Congress*, 2002, vol. 38 Supp., P-1006, (available online at http://altweb.jhsph.edu/publications/journals/iva/iva38_suppl/iva38suppl9a.htm).

Edwards et al. "A Simple And Rapid Method For The Protection Of Plant Genomic DNA for PCR Analysis," *Nucleic Acids Research*, 1991, p. 1349, vol. 19, No. 6.

Ge, B. et al. Differential Effects Of Helper Proteins Encoded by the *cry2A* and *cry11A* Operons On The Formation of Cry2A Inclusions in *Bacillus thuringiensis, FEMS Microbiology Letters*, 1998, pp. 35-41, vol. 165.

Gilmore, C.C. et al. "Sulfate Stimulation of Mercury Methylation in Freshwater Sediments," *Environ. Sci. Technol.* 1992, pp. 2281-2287, vol. 26.

Greenplate, J.T. "Quantification of *Bacillus thuringiensis* Insect Control Protein CRY1Ac Over time in Bollgard Cotton Fruit and Terminals," *J. Econ. Entomol.*, 1999, pp. 1377-1383, vol. 92, No. 6.

Guda, C. et al. "Stable Expression Of A Biodegradable Protein-Based Polymer In Tobacco Chloroplasts," *Plant Cell Reports*, 2000, pp. 257-262, vol. 19.

Harada, M. "Minamata Disease: Methylmercury Poisoning in Japan Caused by Environmental Pollution," *Critical Reviews in Toxicology*, 1995, pp. 1-24, vol. 25, No. 1.

Heifetz, P.B. "Genetic Engineering Of The Chloroplast," *Biochimie*, 2000, pp. 655-666, vol. 82.

Kanno, A. et al. "A Transcription Map Of The Chloroplast Genome From Rice (*Oryza sativa*)," *Current Genetics*, 1993, pp. 166-174, vol. 23.

Khan, M.S. et al. "Fluorescent Antibiotic Resistance Marker For Tracking Plastid Transformation In Higher Plants," *Nature Biotechnology*, Sep. 1999, p. 910, vol. 17.

Kota, M. et al. "Overexpression of the *Bacillus thuringiensis* (Bt) Cry2Aa2 Protein In Chloroplasts Confers To Plants Against Susceptible And Bt-Resistant Insects," *Proc. Natl. Acad. Sci. USA*, Mar. 1999, pp. 1840-1845, vol. 96.

Ma, J.K.-C. et al. "Generation And Assembly Of Secretory Antibodies In Plants," *Science*, May 5, 1995, p. 716(4), vol. 268, No. 5211.

Mayfield, S.P. et al. "Expression And Assembly Of A Fully Active Antibody in Algae," *PNAS*, Jan. 21, 2003, pp. 438-442, vol. 100, No. 2.

McBride, K. et al. Amplification of a Chimeric *Bacillus* Gene In Cloroplasts Leads to an Extraordinary Level of an Insecticical Protein in Tobacco, *Biotechnology*, Apr. 1995, pp. 362-365, vol. 13.

Moar, W.J. et al. "Development of *Bacillus thuringiensis* CrylC Resiistance by *Spodoptera exigua* (Hübner) (Lepidoptera: Naoctuidae)," *Applied and Environmental Microbiology*, Jun. 1995, pp. 2086-2092, vol. 61, No. 6.

Moar, W.J. et al. "Insecticidal Activity of the CryIIA Protein from the NRD-12 Isolate of *Bacillus thuringiensis* subsp. *kurstaki* Expressed in *Escherichia coli* and *Bacillus thuringiensis* and in a Leaf-Colonizing Strain of *Bacillus cereus*," *Applied and Environmental Microbiology*, Mar. 1994, pp. 896-902, vol. 60, No. 3.

Nawwrath, C. et al. "Targeting Of The Polyhydroxybutyrate Biosynthetic Pathway To The Plastids Of *Arabidopsis thaliana* Results In High Levels Of Polymer Accumulation," *Proc. Natl. Acad. Sci. USA*, Dec. 1994, pp. 12760-12764, vol. 91.

Puchta, H. "Removing Selectable Marker Genes: Taking The Shortcut." *Trends in Plant Science* 2000. pp. 273-274, vol. 5, No. 7.

Rashid, A. et al. "Protective Role of $CaCl_2$ Against $Pb^{2+}$ Inhibition in Photosystem II," *FEBS* Oct. 1990, vol. 271, No. 1, 2, pp. 181-184.

Rugh, C.L. et al. "Mercuric Ion Reduction And Resistance In Transgenic *Arabidopsis thaliana* Plants Expressing A Modified Bacterial *merA* Gene," *Proc. Natl. Acad. Sci. USA* Apr. 1996, vol. 93, pp. 3182-3187.

Ruiz, O.N. et al. "Phytoremediation of Organomercurial Compounds via Chloroplast Genetic Engineering," *Plant Physiology* Jul. 2003, vol. 132, pp. 1-9.

Salt, D.E. et al. "Phytoremediation," *Ann. Rev. Plant. Physiol. Plant. Mol. Biol.* 1998, vol. 49, pp. 643-668.

Sidorov, V.A. et al. "Stable Chloroplast Transformation in Potato: Use Of Green Fluorescent Protein As A Plastid Marker," *The Plant Journal* 1999, vol. 19, No. 2, pp. 209-216.

Summers, A. et al. "Microbial Transformations of Metals," *Ann. Rev. Microbiol.* 1978, vol. 32, pp. 637-672.

Summers, A. "Organization, Expression, And Evolution Of Genes For Mercury Resistance," *Ann. Rev. Microbiol.*, 1986, vol. 40, pp. 607-634.

Svab, Z. et al. "High-Frequency Plastid Transformation In Tobacco By Selection Ofr Chimeric *aada* Gene," *Proc. Natl. Acad. Sci. USA*, Feb. 1993, pp. 913-917, vol. 90.

Turkec, A. "Chloroplast Transformation Of Mosquitocidal *Bacillus sphaericus* Binary Toxin Genes In *Chlamydomonas Reinhardtii*," *J. Field Crops*, 1999, pp. 85-90, vol. 4.

Yamamoto, T. et al. "Two types of Entomocidal Toxins in the Parasporal Crystals of *Bacillus thuringiensis kurstaki*," *Achive Biochem. Biophys.*, 1988, pp. 233-241, vol. 227.

Ye, Xudong, et al. "Engineering the Provitamin A (β-Carotene) Biosynthetic Pathway into (Carotenoid-Free) Rice Endosperm," *Science*, 2000, pp. 303-305, vol. 287.

Zoubenko, O.V. et al. "Efficient Targeting Of Foreign Genes Into The Tobacco Plastid Genome," *Nucliec Acid Research*, 1994, pp. 3819-3824, vol. 22, No. 19.

Bizily, S. P. et al. "Phytodetoxification Of Hazardous Organomercurials By Genetically Engineered Plants", *Nature Biotechnology*, Feb. 2000, pp. 213-217, vol. 18.

Crickmore, N. et al. "Involvement of a Possible Chaperonin in the Efficient Expression of a Cloned CryIIA δ-endotoxin gene in *Bacills thuringiensis*", *Molecular Microbiology*, 1992, pp. 1533-1537, vol. 6, No. 11.

Daniell, H. et al. "Containment of Herbicide Resistance Through Genetic Engineering of the Chloroplast Genome", *Nature Biotechnology*, Apr. 1998, pp. 345-348, vol. 16.

Daniell, H. "New Tools for Chloroplast Genetic Engineering", *Nature Biotechnology*, Sep. 1999, pp. 855-856, vol. 17.

Daniell, H. et al. "Transient Expression of β-glucuronidase in Different Cellular Compartments Following Biolistic Delivery of Foreign DNA into Wheat Leaves and Calli", *Plant Cell Rep.*, 1991, pp. 615-619, vol. 9.

Staub, J.M. et al. "High-Yield Production of a Human Therapeutic Protein in Tobacco Chloroplast", *Nature Biotechnology*, Mar. 2000, pp. 333-338, vol. 18.

Peerenboom, E. "German Health Minister Calls Time Out for Bt Maize", *Nature Biotech.*, 2000, p. 374, vol. 18.

Daniell, H. et al. "Marker Free Transgenic Plants: Engineering the Chloroplast Genome Without the Use of Antibiotic Selection", *Curr. Genet.*, 2001, pp. 109-116, vol. 39.

Compeau, G. C. et al. "Sulfate-Reducing Bacteria: Principal Methylators of Mercury in Anoxic Estuarin Sediment", *Appl. Environ. Microbiol.*, Aug. 1985, pp. 498-502, vol. 50, No. 2.

Crickmore, N. et al. "Use of an Operon Fusion to Induce Expression and Crystallisation of a *Bacillus thruingiensis* δ-endotoxin Encoded by a Cryptic Gene", *Mol. Gen. Genet.*, 1994, pp. 365-368, vol. 242.

Sanford, J. C. et al. "Optimizing the Biolistic Process for Different Biological Applications", *Methods Enzymol.*, pp. 483-509, vol. 217.

Daniell, H. "Foreign Gene Expression in Chloroplasts of Higher Plants Mediated by Tungsten Particle Bombardment", *Methods Enzymol.*, 1993, pp. 536-556, vol. 217.

Sambrook *Molecular Cloning*, 1989, Cold Spring Press, Cold Spring Harbor, NY [copy not provided].

*Peptides: Design, Synthesis, and Biological Activity*, 1994, Basava, F. and Anantharamaiah, G. M., Eds, Birkhauser Boston. [copy not provided].

*Protein Folding: Deciphering the Second Half of the Genetic code*, 1990, Gierasch, L. M. and King, J., Eds. American Association for the Advancement of Science. [copy not provided].

Roy, H. S. "RuBisCo: Genes, Structure, Assembly and Evolution", *The Photosynthetic Apparatus*, 1994, pp. 347-364, L. Bogarad, L. Vasil, Eds., Academic Press, NY. [copy not provided].

\* cited by examiner

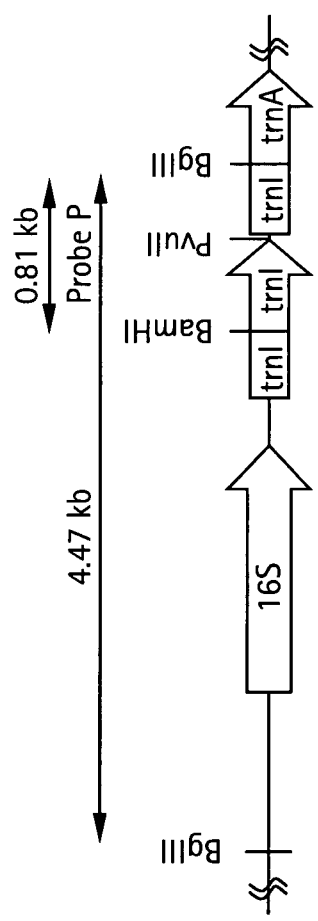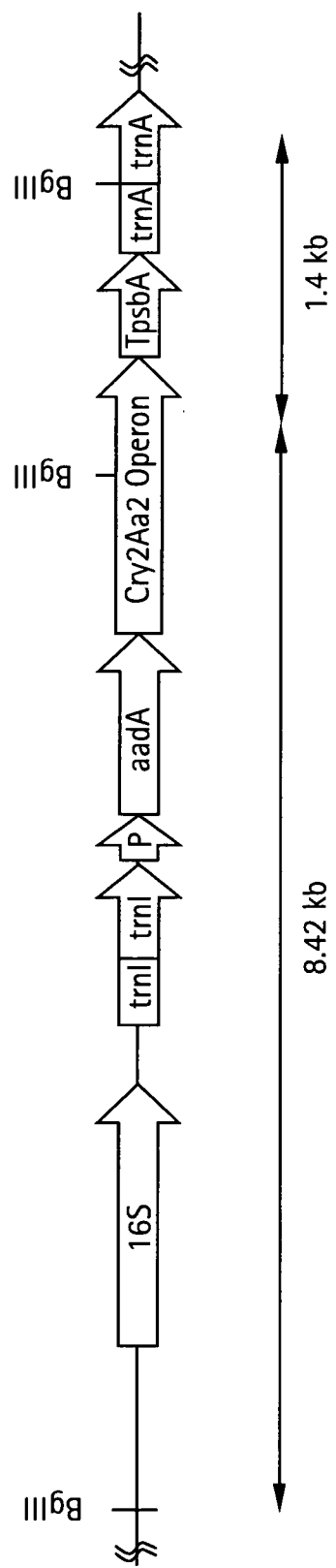
FIG. 2A
FIG. 2B

Cry2Aa2 Single Gene Expression

Cry2Aa2 Operon Expression

FIG. 9A    FIG. 9B    FIG. 9C
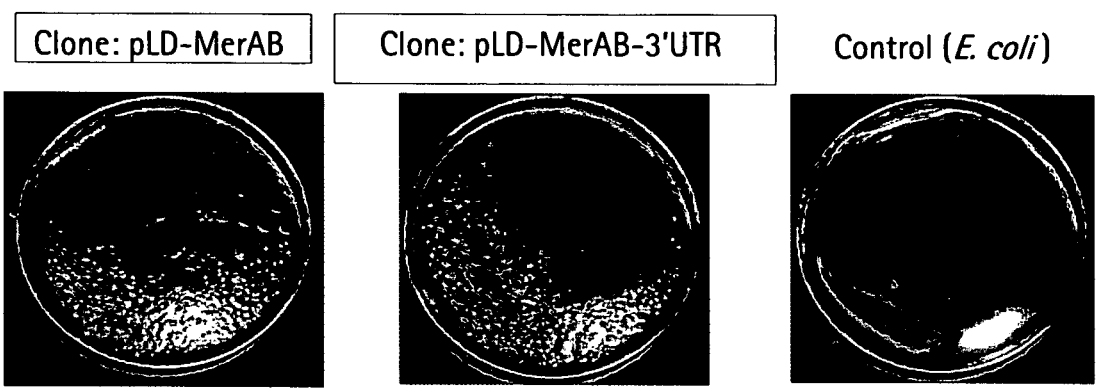
FIG. 10A    FIG. 10B    FIG. 10C
 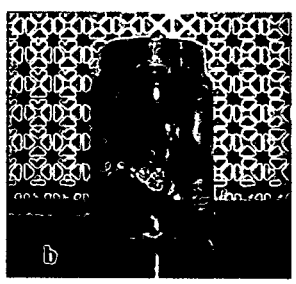 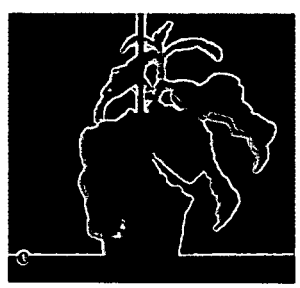

Lemna

M: 1 kb ladder
1: Lemna:3P/trnA3'
2: Tobacco 3P/trnA3'
3: Lemna:Os6P/Os6M
4: 1μl Total DNA Lemna
5: 1μl Total DNA Tobacco pCR21 – Lemna Ct-Border
SmaI/EcoRV C: Correct Sugarcane M: 1 kb ladder
1: Q117:3P/trnA3'
2: Q124 3P/trnA3'
3: Q155:3P/trnA3
4: Tobacco 3P/trnA3' pCR21-Sugarcane Ct-Border
SmaI/EcoRV

US 7,294,506 B2

TOBACCO CHLOROPLAST TRANSFORMATION VECTORS COMPRISING A MULTI-GENE OPERON ENCODING A BIOPHARMACEUTICAL PROTEIN AND A CHAPERONIN

CROSS-REFERENCE TO RELATED APPLICATION(S)

The present application is a continuation of U.S. Ser. No. 09/807,723, filed Apr. 18, 2001 now abandoned which was the National Stage of International Application No. PCT/US01/06276, filed Feb. 28, 2001, which claims the benefit of U.S. Provisional Application No. 60/266,121, filed Feb. 2, 2001, and the benefit of U.S. Provisional Application No. 60/259,248, filed Dec. 29, 2000, and the benefit of U.S. Provisional Application No. 60/257,408, filed Dec. 22, 2000, and the benefit of U.S. Provisional Application No. 60/185,660, filed Feb. 29, 2000; all of which are hereby incorporated by reference herein in their entirety, including any figures, tables, nucleic acid sequences, amino acid sequences, or drawings.

STATEMENT REGARDING FEDERALLY SPONSORED FEDERAL RESEARCH

The work of this invention is supported in part by the USDA-NRICGP grants 95-82770, 97-35504 and 98-0185 to Henry Daniell.

FIELD OF INVENTION

This application pertains to the field of genetic engineering of plant genomes, particularly plastids and to methods of and engineered plants with operons that lead to and result in overexpression of the gene of interest. This application also pertains to the field of genetic engineering of algal and bacterial genomes.

DESCRIPTION OF RELATED ART

Karamata, in U.S. Pat. No. 4,797,279, proposed the generation of *Bacillus thuringiensis* hybrids that have insecticidal properties through conjugation. Conjugation is mediated by a conjugative plasmid functional in the B.t. kurstaki strain and the B.t. tenebrionis strain. The resulting hybrid is capable of producing each of the delta-endotoxin crystals typical for a B.t. kurstaki strain and a B.t. tenebrionis strain.

McBride, in U.S. Pat. No. 5,545,818 and McBride et. al. (1995), describes a method of 26 genetically engineering the plastids of a plant or plant cell such they provide increased expression of the *Bacillus thuringiensis* insecticidal proteins in the plastids. A construct containing a promoter functional in plant plastids, a single gene encoding an insecticidal *Bacillus thuringiensis* toxin, another DNA sequence encoding a selectable marker, and a transcription termination region capable of terminating transcription in a plant plastid, is used to affect plant transformation. The transcription and translation of the B.t. gene product occurs in the plastids.

Daniell et. al., in U.S. Pat. No. 5,932,479 (1999), entitled "Genetic engineering of plant chloroplast," teaches plant cells chloroplast transformed by means of an expression cassette comprising an exogenous DNA sequence which is stably integrated to the chloroplast genome of the cell of a target plant. "Stably" integrated DNA sequences are those which are inherited through genome replication by daughter cells or organisms. This stablility is exhibited by the ability to establish permanent cell lines, clones, or transgenic plants comprised of a population containing the exogenous DNA.

Likewise, U.S. Pat. No. 5,693,507 (1997) to Daniell and McFadden discloses such stable integration of the chloroplast by means of an expression cassette which comprises an exogenous DNA sequence which codes for a desired trait, and the transformed plant.

Daniell, in PCT International Publication WO 99/10513, teaches the composition and use of universal chloroplast integration and expression by vectors to stably transform and integrate genes of interest into chloroplast genome of multiple species of plants. This leads to chloroplast expression of genes of interest. Transformed plants show the highest level of expression. Plants transformed with insecticidal genes are lethal to insects that are 40,000-fold resistant to Bt. insecticidal proteins.

Significantly, in the prior art inventions use multiple promoters to drive the expression of multiple genes. Put differently, the inventions of the prior art employ a single promoter to drive a single monocistron. In contrast, the present invention employs a single promoter to drive polycistrons, resulting in equal levels of expression of the polycistrons.

All publications and patents are hereby incorporated by reference.

BACKGROUND OF THE INVENTION

In plant and animal cells, nuclear mRNAs are translated monocistronically. This poses a serious problem when engineering multiple genes in plants. Therefore, in order to express the polyhydroxybutyrate polymer or Guy's 13 antibody, single genes were first introduced into individual transgenic plants, then these plants were back-crossed to reconstitute the entire pathway or the complete protein. Similarly, in a seven year-long effort, Ye et. al. recently introduced a set of three genes for a short biosynthetic pathway that resulted in β-carotene expression in rice. In contrast, most chloroplast genes of higher plants are co-transcribed. Multiple steps of chloroplast mRNA processing are involved in the formation of mature mRNAs.

In accordance of the invention expression of polycistrons via the plastid genome, in particular the chloroplast genome, provides a unique opportunity to express entire pathways in a single transformation event. Additionally, chloroplast genetic engineering is an environmentally friendly approach resulting in containment of foreign genes and hyper-expression.

Plant bioremediation (phytoremediation), is the use of plants for in-situ restoration of contaminated sites. The technique has risen in the last decade as a strong and safe technique to address with the increasing problems of the pollution of soil and water bodies. In the past other techniques, such as mechanical and bacterial bioremediation were implemented with little success, since they were costly and threatened the safety of our environment. Plants, on the other hand, are advantageous for bioremediation systems since they have a high capacity for adaptation to different environments and a natural resistance against different toxic pollutants. They are cheap, non-evasive and help contain disrupted ecosystems. These characteristics make plants an ideal vehicle for bioremediation.

Mercury is a toxic heavy metal that is commonly released into the environment as a byproduct of different chemical reactions of modem industries. The present world production of mercury is about 9000 tons/year (http://www.chem.ualberta.cal.htm). In the environment, mercury is rapidly methylated by methanogenic bacteria (Ex. *Desulfovibrio desulfuricans*) producing the 10 fold more toxic organomercurials (Compeau et. al.) 1985; Gilmour et. al. 1992). Organomercurials are more toxic due to its increased hydrophobicity, which allows it to cross lipid membranes because it is more hydrophobic than mercury. Over 90% of the intake of methylmercury is absorbed into blood compared with only 2% of inorganic mercury (http://www.chem.ualberta.cal.htm). Both organomercurials and mercury have the tendency to accumulate in the tissue, especially in the membrane bound organelles. In plants organic mercury crosses the lipid membrane of organelles, for example chloroplast, where it can poison essential oxidative and photosynthetic electron transport chains more easily than metallic mercury (Rugh et. al. 1996). In photosynthetic organisms, mercuury affects the oxygen-evolving complex that is found in the photosystem II and is bound to the thylakoid membrane (Bernier et al. 1993). Mercury treatment of PSII leads to a strong inhibition of oxygen evolution by removal of EP33 (one of the proteins of the OEE complex; Bernier et al. 1995). Mercury reduces the Fm and Fv values due to additional inhibitory sites on the donor side of PSII, including damage to the light-photochemistry (Rashid et al. 1990). Medical researchers discovered that high levels of methylmercury cause severe neurological degeneration in birds, cats and humans (Minamata Disease Research Group, 1968; Harada et. al. 1995). Thus, mercury and organomercurials are ideal targets for phytoremediation.

In water, mercury pollution also poses a problem. Mercury accumulates in the sediments of lakes and oceans where methanogenic bacteria live (http://ehpnet.niehs.nih.gov). These bacteria methylate mercury to produce methylmercury, which is eventually released into water (Harada et al. 1995). The methylmercury is trapped into the small fish when the water passes through their gills or they feed on phytoplanktons that carry high concentrations of the pollutant. Predatory fish, as bass in fresh water and tuna in salt water, live for long periods of time feeding on smaller fish. During their life span, they can accumulate high levels of methylmercury that can reach 1.0 ppm in normal water and 30 ppm in areas of high pollution with mercury (http://ehpnet.niehs.nih.gov). Then, humans and birds feed on contaminated fish and accumulation in their tissue cause severe neurological damage.

Meagher and colleagues have used a nuclear modified form of the merA and merB genes to transform plants that are resistant to mercury and organomercurials respectively (Bizily et al. 1999; Rugh et. al. 1996), U.S. Pat. No. 5,965,796 (1999). One of the drawbacks of nuclear genetic engineerig is that it requires several back crosses to create the complete pathway that detoxifies mercury and organomercurials (Bizily et al. 2000). This results in variation in expression levels among different transgenic lines and tolerance to different concentrations of organomercurials, only in low levels of tolerance (10 µM) (Bizily et al. 2000). Another concern of the use of nuclear transformed plants in-situ is the escape of the foreign genes via pollen (Daniell 1999; Bogorad, 2000);

The present invention provides a transgenic plant bioremediation system for soil as well as a transgenic algae/bacteria bioremediation system for water.

Non-obviousness of Expression of Operons via the Chloroplast Genome

Despite the potential advantages of chloroplasts for foreign gene expression, it was not obvious that multiple genes expressed by a single promoter in chloroplasts would be expressed in this organelle in a coordinated manner. Polycistrons have been observed in chloroplasts in the past but processing RNA sequences present in between individual transcripts, proteins or enzymes involved in processing or cofactors necessary for processing of polycistrons have not yet been characterized. Therefore, it was not obvious to one skilled in the art that multiple foreign gene transcripts would be properly processed and translated when expressed from a heterologous promoter.

Prior to this patent application there were no published reports of expression of multiple genes in chloroplasts and there were valid reasons to suggest that it would be problematic. Indeed, despite several reports of foreign gene expression via the chloroplast genome, no one ever attempted expression of a bacterial operon via the chloroplast genome because of inadequate understanding of processing of polycistrons within plastids. All foreign genes engineered via the plastid genome have been driven by individual promoters and 3' regulatory sequences. It was not known whether 3' terminators and regulatory sequences were necessary for individual genes of the foreign operon. It is generally believed that the proteins or enzymes involved in processing may be under the control of the nuclear genome. It was also believed that there may be several environmental factors involved in processing polycistrons, including light.

While chloroplast ribosome binding sites have been characterized, it was not obvious that ribosome binding sites or untranslated regions upstream of bacterial genes would function in plastids. Also, it was not anticipated that a chaperonin present in a bacterial cell would function within chloroplasts and help fold the foreign protein or interfere with folding of other chloroplast proteins. It was certainly unanticipated that it was possible to create cuboidal crystals within chloroplasts duplicating the functions of a bacterium during sporulation or duplicate bioremediation pathways within plastids. There was no certainty that the enzymes of the pathway or proteins of the operon would be expressed in a coordinated manner.

Indeed, the prior art suggested that there might have been unforeseen deleterious effects of high-level expression of several foreign proteins within chloroplasts on plant growth or development that were not apparent from the experiences with other transgenes. The pH and oxidation state of the chloroplast differs from that of bacterial cells in ways that might inhibit or prevent functions of proteins or enzymes. Because the results of this invention contradicted those teachings of the prior art, this invention was characterized as breakthrough in plant biotechnology and featured on the cover of Nature Biotechnology (the most prestigious biotechnology journal in the world) in January 2000. Scientists around the world have written reviews subsequent to that publication appreciating this invention. Engineering multiple genes in transgenic plants via the nuclear genome is not only extremely time consuming (taking several years to accomplish) but is riddled with problems of position effect, gene silencing etc. Therefore, this accomplishment was characterized as the holy-grail of plant biotechnology.

SUMMARY OF THE INVENTION

By this invention, plastid expression constructs are provided which are useful for genetic engineering of plant cells and which provide for enhanced expression of several foreign proteins in plastids utilizing a single transformation event. The transformed plastid is preferably a metabolically active plastid, such as the chloroplasts found in green and non-green plant tissues including leaves and other parts of the plant. This invention opens the door to engineering novel pathways for metabolic engineering and gene stacking, or for multi subunit complex proteins requiring stoichiometric and coordinated expression of multiple genes. The plastid is preferably one which is maintained at a high copy number in the plant tissue of interest.

The present invention is applicable to all plastids of plants. These include chromoplasts which are present in the fruits, vegetables and flowers; amyloplasts which are present in tubers like the potato; proplastids in roots; leucoplasts and etioplasts, both of which are present in non-green parts of plants.

The plastid expression constructs for use in this invention generally include a single plastid promoter region and multiple genes of interest to be expressed in transformed plastids. The DNA sequence of interest may contain a number of consecutive encoding regions, to be expressed as an operon, for example where introduction of a foreign biochemical pathway into plastids is desired for metabolic engineering or gene stacking. Plastid expression constructs of this invention is linked to a construct having a DNA sequence encoding a selectable marker which can be expressed in a plant plastid.

In a preferred embodiment, transformation vectors for transfer of the construct into a plant cell include means for inserting the expression and selection constructs into the plastid genome. This preferably comprises regions of homology to the target plastid genome which flank the constructs.

The chloroplast vector or constructs of the invention preferably include a universal chloroplast expression vector which is capable of importing a desired trait to a target plant species. Such a vector is competent for stably transforming the chloroplast genome of different plant species which comprises an expression cassette which is described further herein. Such a vector generally includes a plastid promoter region operative in said plant cells chloroplast, a gene which is linked to a multi-gene operon which includes an ORF which codes for a putative chaperonin which facilitates the folding of the protein to form proteolytically stable cuboidal crystals. Preferably, one or more DNA sequences of interest to be expressed in the transformed plastids.

The invention provides also a plastid vector comprising of a DNA construct. The DNA construct includes a 5' part of a plastid DNA sequence inclusive of a spacer sequence; a promoter that is operative in the plastid; at least a heterologous DNA sequence encoding multiple peptides of interest; a gene that confers resistance to a selectable marker; a multi-gene operon; a transcription termination region functional in the target plant cells; and a 3' part of the plastid DNA sequence inclusive of a spacer sequence. The DNA construct is flanked by DNA sequences which are homologous to the spacer sequence of the target plastid genome. The plastid is preferably a chloroplast. The vector preferably includes a ribosome binding site and a 5' untranslated region (5'UTR). A promoter operative in the green and non-green plastids is to be used in conjunction with the 5'UTR, The invention provides a promoter that is operative in the green and non-green plastids of the target plant cells such as the psbA promoter, rbcL promoter, atpp promoter region, accD promoter, and the 16SrRNA promoter.

The invention provides a gene, which can be a mutant gene, that confers resistance, such as antibiotic resistance, to a selectable marker like the aadA gene.

The invention provides a cassette which can be modified to include a selectable marker, a gene encoding the chaperonin and any desired heterolgous gene. Such applications will be beneficial for the high level production in plants of other desired protein products as well.

Further, the invention preferably provides a three-gene insecticidal *Bacillus thuringiensis* (Bt) operon which shows operon expression and crystal formation via the chloroplast genome. The operon comprises of three operably linked components which operate in concert as a biosynthetic pathway: a distal gene which codes for a insecticidal protein and two open reading frames (ORF). The two ORFs code for at least one molecule of interest and at least one chaperonin to assist in the folding of the insecticidal protein. The molecule of interest of this operon can be a peptide, an enzyme, a selectable marker, or a bio-pharmaceutical, including monoclonals.

This invention also provides for other three-gene operons, particularly insecticidal operon or the Cry2Aa2 operon. This invention also provides for operons of the Cry or Cyt series.

An operon of this invention further provides that the second ORF (ORF2) codes for a putative chaperonin. A chaperonin is a molecule which facilitates the folding and assembly of proteins to form functional proteolytically stable cuboidal crystals. The ORF2 is operably linked to a gene encoding the insecticidal protein. The invention provides a bacterial chaperonin that is capable of facilitating the folding and assembly of insecticidal proteins.

This invention also provides crystalized insecticidal proteins such as 6-endotoxin proteins, Cry proteins such as the Cry2Aa2 proteins, or Cyt proteins.

In accordance of the invention, the introduction blocks of foreign genes in a single operon would avoid complications inherent in nuclear transformation such as position effect and gene silencing in putting one gene at a time into random locations in the nuclear genome. Repeated use of a single promoter causes gene silencing (De Wilte, C. et. al. 2000). Cloning several genes into a single T-DNA does not-avoid the compounded variable expression problem encountered in nuclear transgenic plants. This invention shows that a bacterial operon can be expressed in a single integration event. Expression of multiple genes via a single transformation event opens the possibility of expressing foreign pathways or pharmaceutical proteins involving multiple genes.

The invention provides for the demonstration of expression of a bacterial operon or polycistrons in transgenic plants and opens the door to engineer novel pathways in plants in a single transformation event.

The invention provides a single vector or construct (or cassette) which encodes more than one heterologous protein product. This embodiment of the invention provides that a heterologous DNA fragment that is introduced into a universal vector encodes more than one gene. In one example shown, this invention discloses, the DNA encodes an operon of three genes and produces proteins from at least two genes, one of those genes encode a protein and a chaperone protein. This aspect of the invention—to co-expressing multiple genes—is beneficial if one skilled in the art desires to introduce a biosynthetic pathway that comprises multiple steps into plants. For example, a three step synthesis of a desired compound might require three different enzymes. A single transformation will generate a recombinant plant possessing all three heterologous enzymes which can function in concert to produce the desired product.

Thus another embodiment of the invention relates to the maximal production of a heterologous protein by co-expressing it with another polypeptide that induces crystallization of said protein. This aspect of the invention provides the yield of heterologous gene expression is greatly enhanced if the desired protein is in crystal form in the transformed plant. The increased yield is because the crystal form of the proteins protected them from cellular proteases. This is accomplished by co-expressing the desired gene with a second gene encoding a chaperonin that directs crystallization.

Also, formation of crystals of foreign proteins opens a simple method of purification via centrifugation. Plants transformed with the cry2Aa2 operon of the invention show a large accumulation and improved persistence of the expressed insecticidal protein(s) throughout the life of the plant. This is most likely because of the folding of the insecticidal protein into cuboidal crystals, thereby protecting it from proteases. This is an environmentally friendly approach because folded crystals improve the safety of the Bt transgenic plants. In contrast to currently marketed transgenic plants that contain soluble CRY proteins, folded protoxin crystals will be processed only by those target insects that have high alkaline gut environment. In addition, absence of insecticidal protein in transgenic pollen eliminates toxicity to non-target insects via pollen. Expression of the cry2Aa2 operon in chloroplasts provides a model system for hyper-expression of foreign proteins in a folded configuration enhancing their stability and facilitating single step purification. This is the first successful demonstration of expression of a bacterial operon in transgenic chloroplast plants.

The invention provides a model system for large-scale production of foreign protein within chloroplasts in the folded configuration enhancing their stability and facilitating single-step purification, for example, biopharmaceuticals such as human serum albumin (HSA) and insulin.

All known methods of transformation can be used to introduce the vectors of this invention into target plant plastids including bombardment, PEG Treatment, *Agrobacterium*, microinjection, etc.

The invention provides transformed crops, like solanaceous plants (monocotyledonous and dicotyledonous). Preferably, the plants are edible for mammals, including humans.

The invention provides target Bt transgenic plants which are likely to show a more stable protein expressed at high levels in the chloroplast throughout the growing season. It should increase toxicity of Bt transgenic plants to target insects and help eliminate the development of Bt resistance. The invention provides an example of the cry2Aa2 bacterial operon is expressed in tobacco chloroplasts to test the resultant transgenic plants for increased expression and improved persistence of the accumulated insecticidal protein(s).

The invention provides transformed plants including leaves which accumulated a high percent of total soluble protein (close to 50%) in mature leaves and remain stable even in old bleached leaves.

The invention provides transformed plants which are resistant to difficult-to-control insects, like cotton boll worm, which were killed 100% after consuming transgenic leaves. The invention also provides plants which contain insecticidal protein fold into cuboidal crystals. Plants which contain protoxin crystals, which will be processed only by target insects that have high alkaline gut environment, which should improve safety of Bt transgenic plants. Also, plants are free of insecticidal proteins in transgenic pollen, which eliminates toxicity to non-target insects via pollen such as Monarch butterfly larvae. The invention provides electron microscopic proof of the presence of the cuboidal crystals inside the chloroplast.

The invention also provides an environment friendly approach to engineering insect resistance to plants because folded crystal products improve the safety of the Bt transgenic plants which will be edible consume, mammals, including humans.

In another embodiment of the invention provides heterologous DNA sequences which mediate resistance to (a) heavy metal in transgenic plants or plant cells which express these coding sequences encoding metal ion reductases and (b) organomercurial compounds in transgenic plants or plant cells which express the coding sequence encoding organomercury lyase. Preferably the coding sequence is that of merA (which encodes mercuric ion reductase) and merB (which encodes organomercury lyase).

The present invention provides a chloroplast universal vector which contains a Mer operon containing metal resistance coding sequences operably linked to transcriptional and translational control sequences which are functional in the chloroplast in target plants. Preferably the coding sequence is that of merA and merB. Also, the present invention provides transgenic plant cells, plant tissue and plants whose chloroplast has been modified to contain and express two metal resistance coding sequences operably linked to transcriptional and translational control sequences which are functional in the chloroplast of target plants. Preferably the coding sequences are that of merA and merB. Also provided by the present invention are methods for effecting metal resistance in plants by stably transforming a plant to contain and express two heterologous DNA sequences encoding metal resistance operably linked to transcriptional and translational control sequences which are functional in the chloroplasts of target plants. Preferably the coding sequence is that of merA and merB.

The present invention are methods for effecting metal resistance in plants by stably transforming a green algae or cyanobacteria to contain and express two heterologous DNA sequences encoding metal resistance operably linked to transcriptional and translational control sequences which are functional in the target green algae or cyanobacteria. Preferably the coding sequence is that of merA and merB.

A further object of the invention are transgenic plants, algae and bacteria which contain and express metal resistance and organomercurial compound resistance coding sequences.

Other embodiments of the invention are described in greater detail hereinafter.

BRIEF DESCRIPTION OF THE DRAWINGS

FIG. 1A shows chloroplast expression vector pLD-BD Cry2Aa2 operon (9.8 kb) with PCR primer landing sites and expected fragment sizes.

FIG. 1B shows PCR analysis of untransformed and putative chloroplast transformants using primer set 1 p1M.

FIG. 1C shows analysis of untransformed and putative chloroplast transformants using primer set 3P3M (lane 1: 1 kb ladder; lane 2: untransformed; lanes 3-7: pLD-BD cry2Aa2 operon putative transformants; and lane 8: pLD-BD cry2Aa2operon plasmid DNA).

FIGS. 2A, 2B, and 2C show the Southern blot analysis of $T_0$ and $T_1$ generations. FIG. 2A shows the 0.81 kb probe BamHl-Bglll fragment containing the chloroplast flanking sequence. Untransformed plants generate a 4.47 kb fragment. FIG. 2B shows a vector map showing Cry2Aa2 operon transformed 32P labeled fragments of 8.42 kb and 1.42 kb. FIG. 2C shows in lane 1:1 kb ladder; lane 2: untransformed; lanes 3-7; T0 transgenic lines; and in lanes 8-9: T1 transgenic lines.

FIG. 3 shows the 10% SDS-PAGE gel stained with R-250 Coornassie Blue. Loaded protein concentrations are provided in parenthesis. Lanes 1: prestained protein standard; Lane 2: partially purified Cry2Aa2 protein from *E. Coli* (5 µg); Lane 3: Single Gene derived Cry2Aa2 pellet extract solubilized in 50 mM NaOH (22.4 µg); Lane 4: Single Gene derived Cry2Aa2 supernatant (66.5 µg); Lane 5: Operon Derived Cry2Aa2 supernatant (58.6 µg); Lane 7: untransformed tobacco pellet extract solubilized in 50 mM NaOH (29.8 µg); Lane 8: untransformed tobacco supernatant (30.4 µg). Colored compounds observed in the supernatant of transgenic plants interfered with the DC Bio-Rad protein assays but not in the pellet.

FIGS. 4A and 4B show the quantification of Single Gene derived Cry2Aa2 and Operon Derived Cry2Aa2 proteins by ELISA as a percentage of total soluble protein in young, mature, and old transgenic leaves. FIG. 4A shows single gene derived Cry2Aa2 expression shown as a percentage of total soluble protein. FIG. 4B shows operon derived Cry2Aa2 expression shown as a percentage of total soluble protein.

FIGS. 5A, 5D, and 5G show the insect bioassays of untransformed tobacco leaves. Plate A was treated with *H. virescens*, plate D was treated with *H. zea*, and plate G was treated with *S. exigua*.

FIGS. 5B, 5E, and 5H show single gene derived cry2Aa2 transformed leaves. Plate B was treated with *H. virescens*, plate E was treated with *H. zea*, and plate H was treated with *S. exigua*.

FIGS. 5C, 5F, and 5I show operon derived cry2Aa2 transformed leaves. Plate C was treated with *H. virescens*, plate F was treated with *H. zea*, and plate I was treated with *S. exigua*.

FIGS. 9A, 9B, and 9C show transformed *E. Coli* grown in 100 µm $H_gCl_2$. Transformed *E. coli* cells containing the vectors pLD-merAB and pLD-MerAB-3'UTR grown in LB at different concentrations of $H_gCl_2$. Plates show transformed cells growing at 100 µM $H_gCl_2$. No growth was observed in the control.

FIGS. 10A, 10B, and 10C show chloroplast transgenic plants. FIG. 10A shows a transgenic plant shoot induction in RMOP with 500 µg/ml Spec. FIG. 10B shows a transgenic plant root induction in MSO with 500 µg/ml Spec. FIG. 10C shows a transgenic plant grown in soil.

Figure 11A:
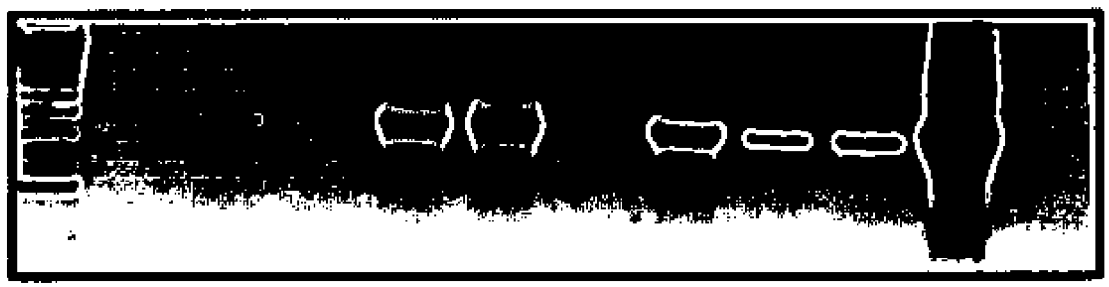
Figure 11B:
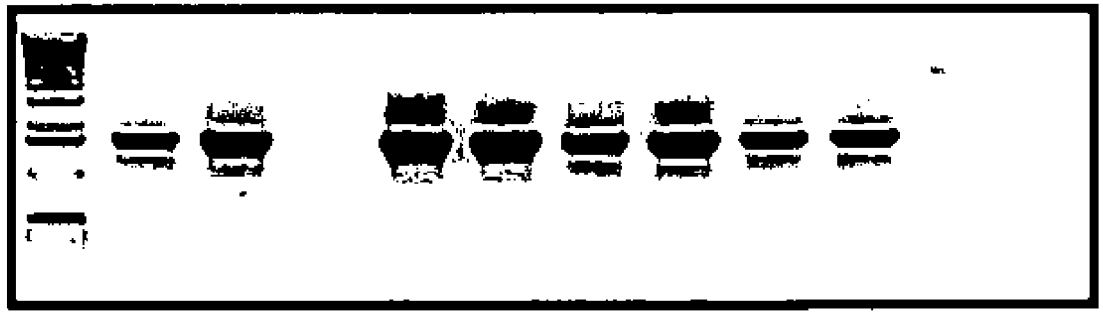

FIGS. 11A and 11B show integration of the mer operon into the chloroplast genome. FIG. 11A shows PCR using specific primers that land in the gene cassette (5P/2M) show a product of 3.8 kb size (clones 2, 4, 5, 7, 9, 11). Clones 1 and 3 show no integration of the cassette. Positive control, is plasmid pLD-merAB-3'UTR. Negative control is untransformed plant DNA. FIG. 11B shows PCR using specific primers that land within the native chloroplast genome (3P/3M), eliminate mutants (cline 3), showing integration of the cassette into the chloroplast genome (clones: 1, 2, 4, 5, 6, 7, 9, 11. 1.6 kb PCR product).

Figure 12:
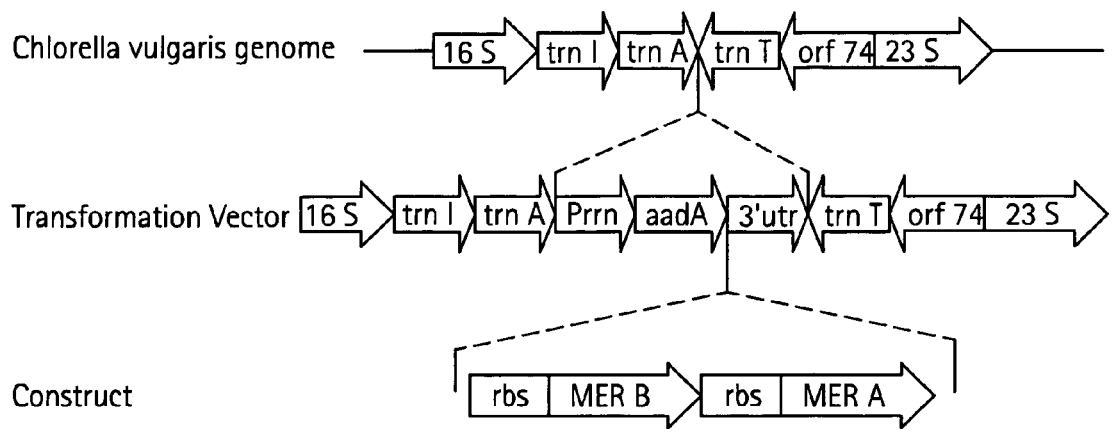

FIG. 12 shows the *Chlorella vulgaris* vector construct.

Figure 13:
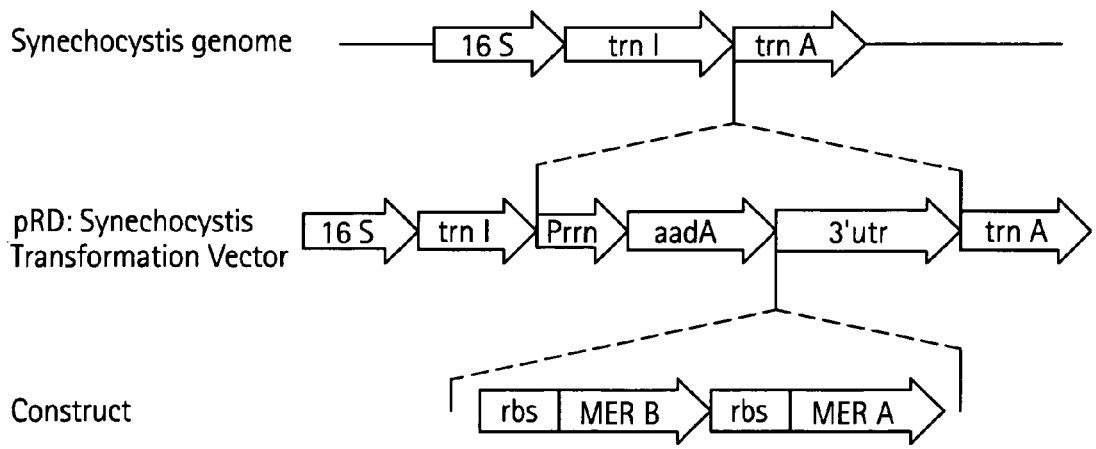

FIG. 13 shows the *Synechocystis* vector construct.

Figure 14:
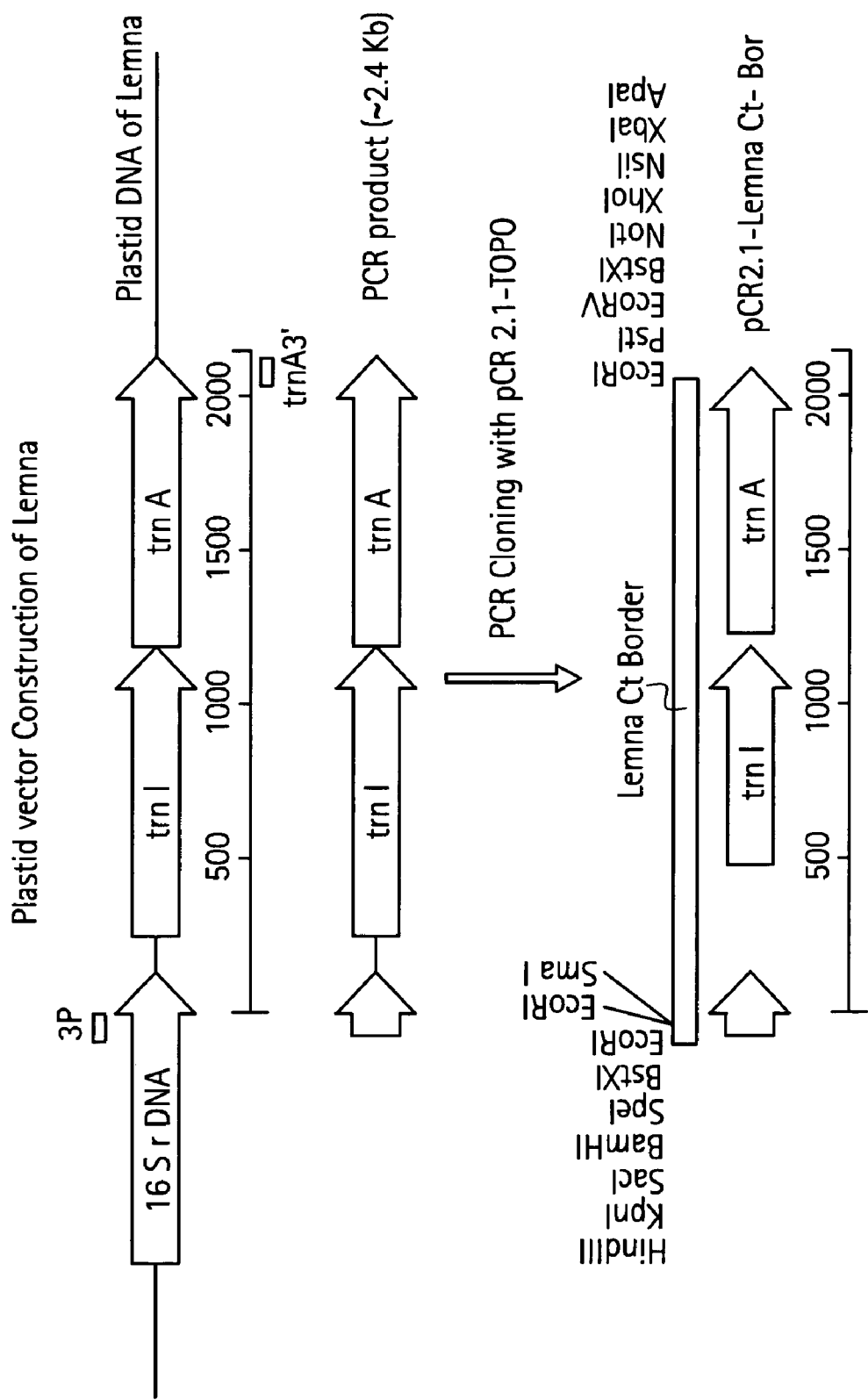

FIG. 14 shows the Lemna vector construct.

Figure 15:
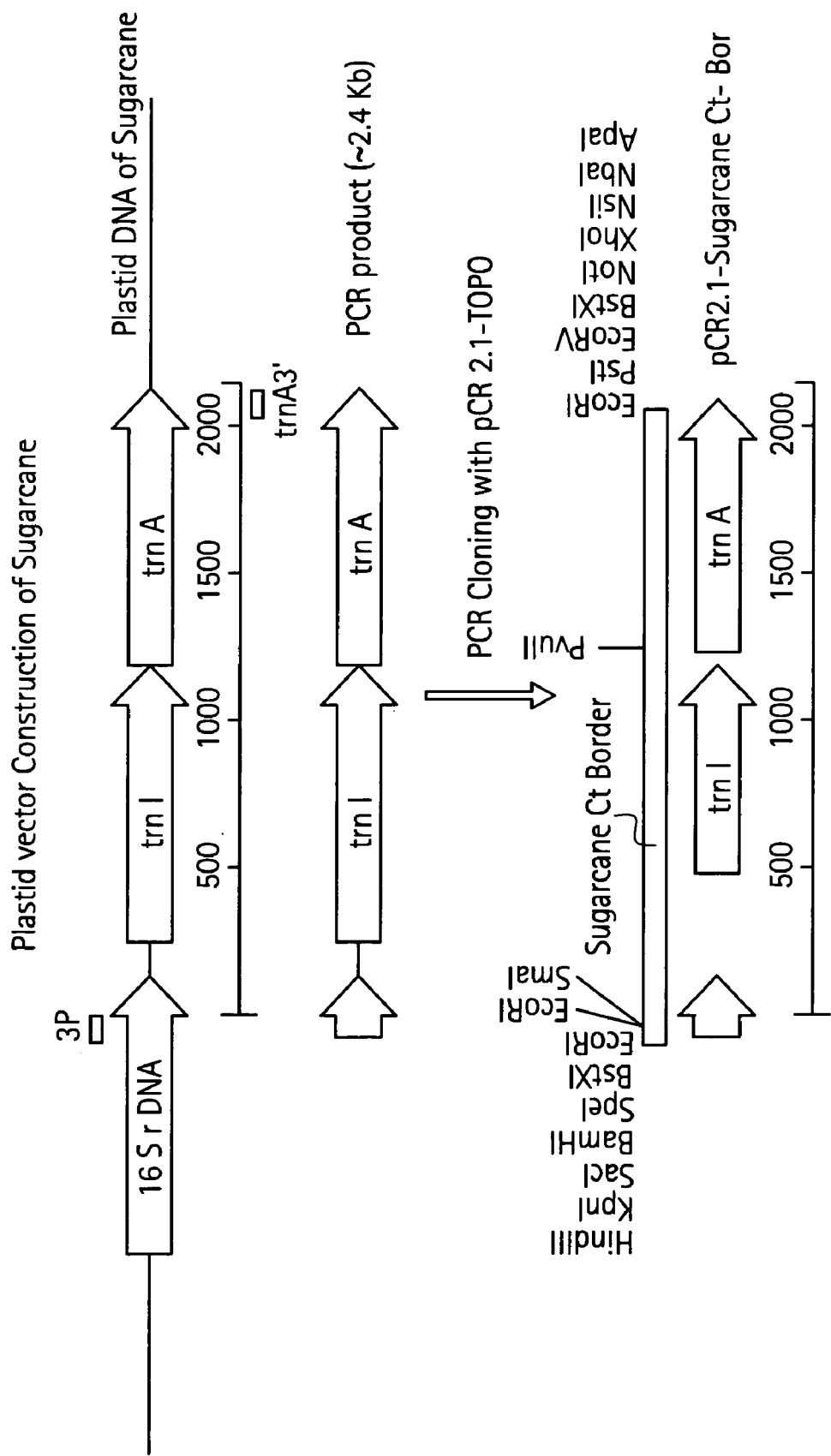
Figure 16A:
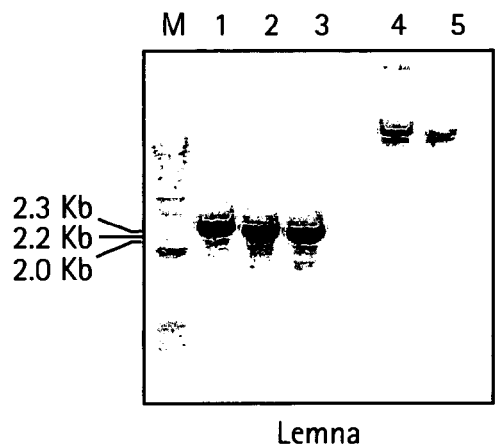
Figure 16B:
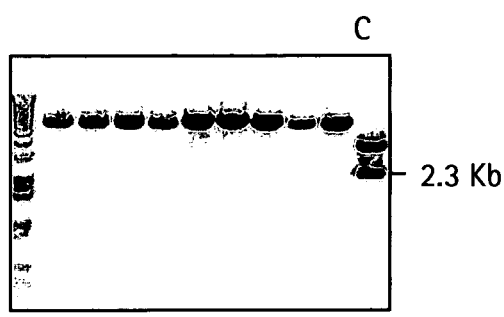
Figure 16C:
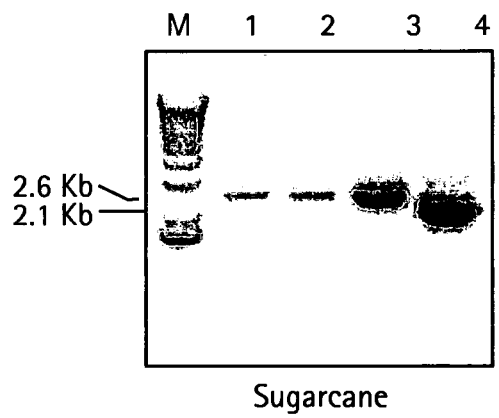
Figure 16D:
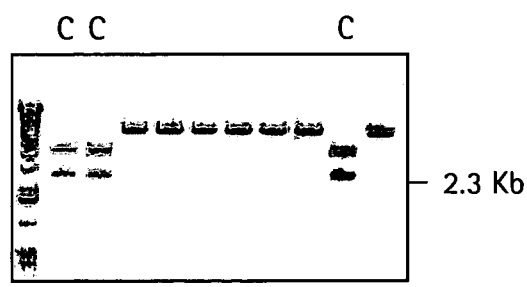

FIG. 15 shows the Sugarcane vector construct.

FIGS. 16A, 16B, 16C, and 16D show confirmation of Lemna vector construct.

Figure 17:
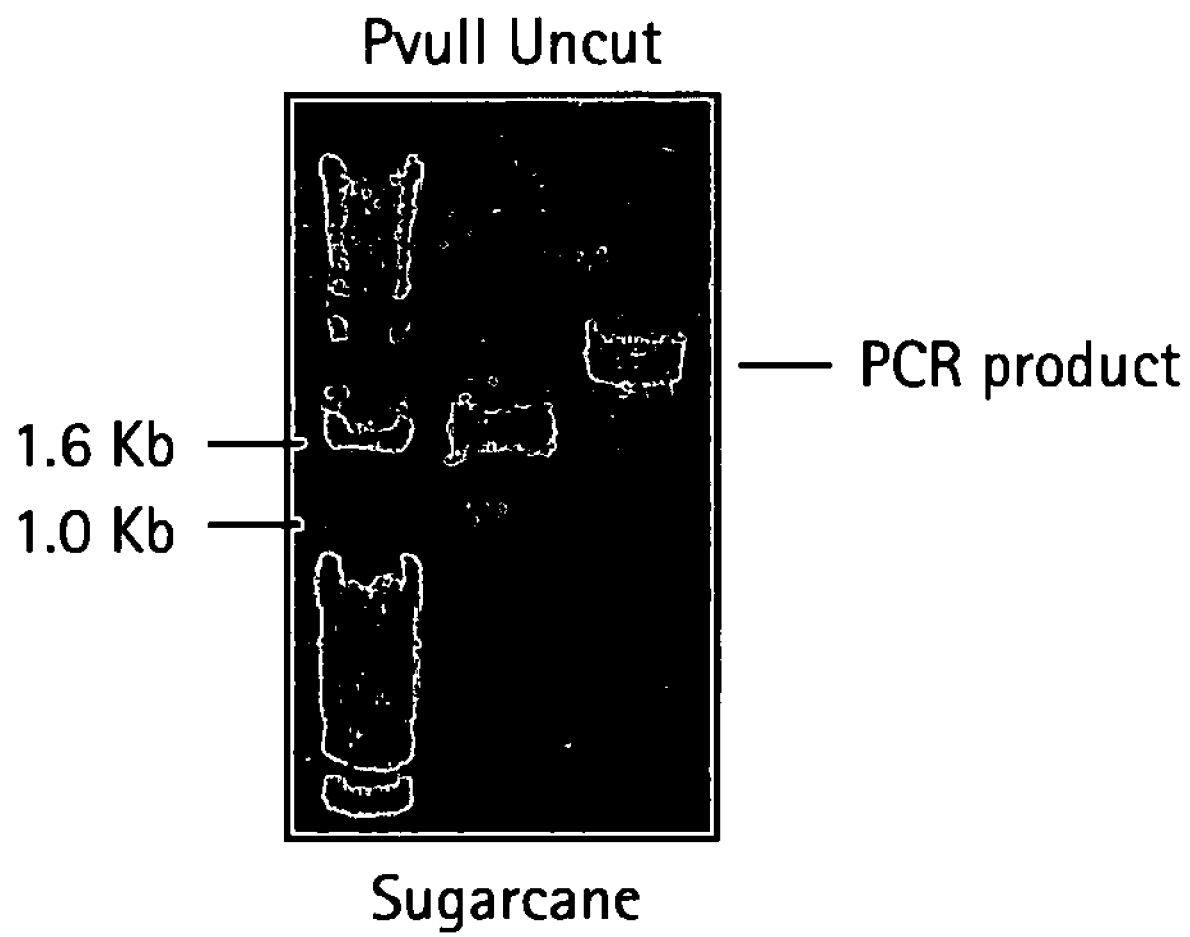

FIG. 17 shows confirmation of Sugarcane vector construct.

Figure 18A:
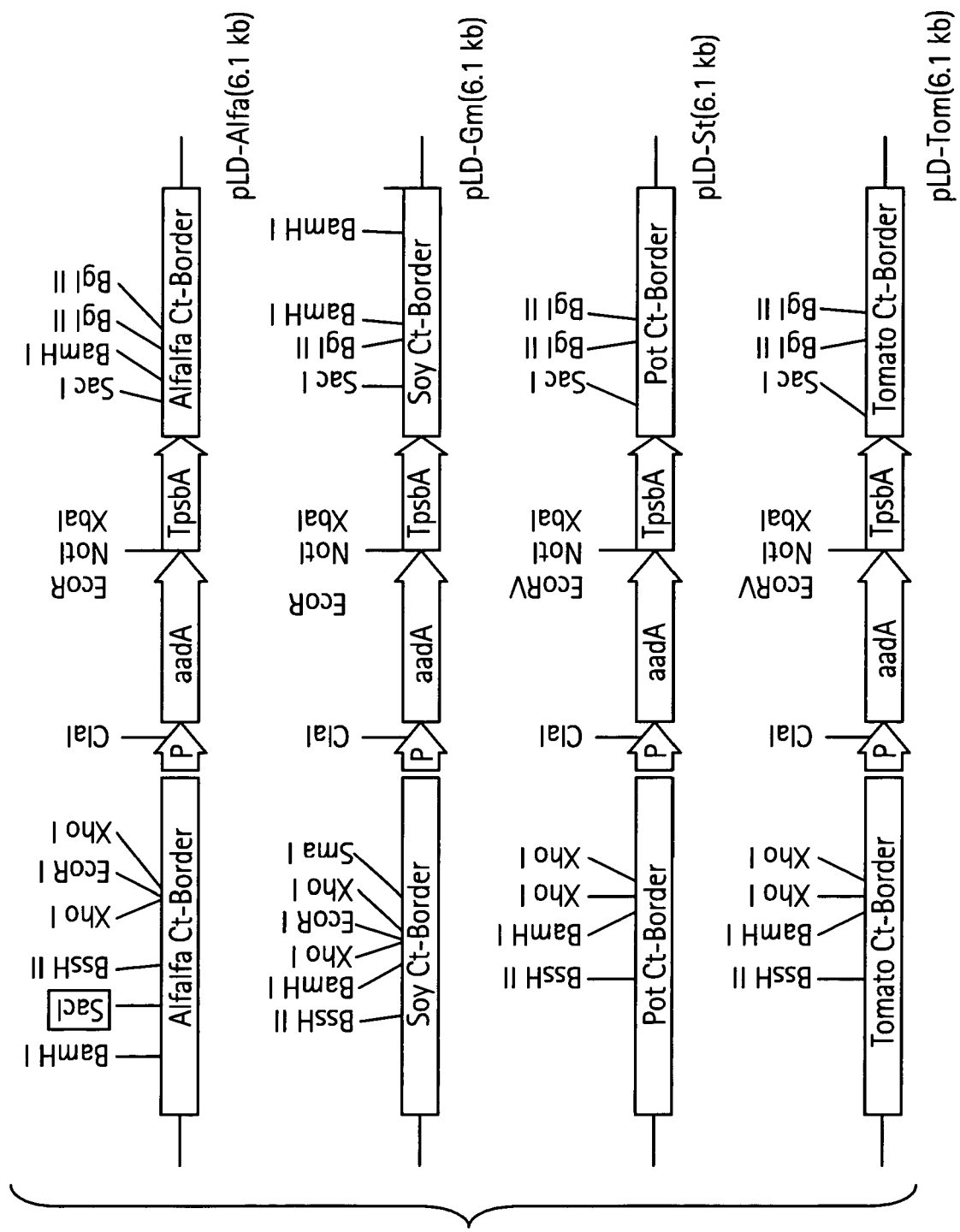
Figure 18B:
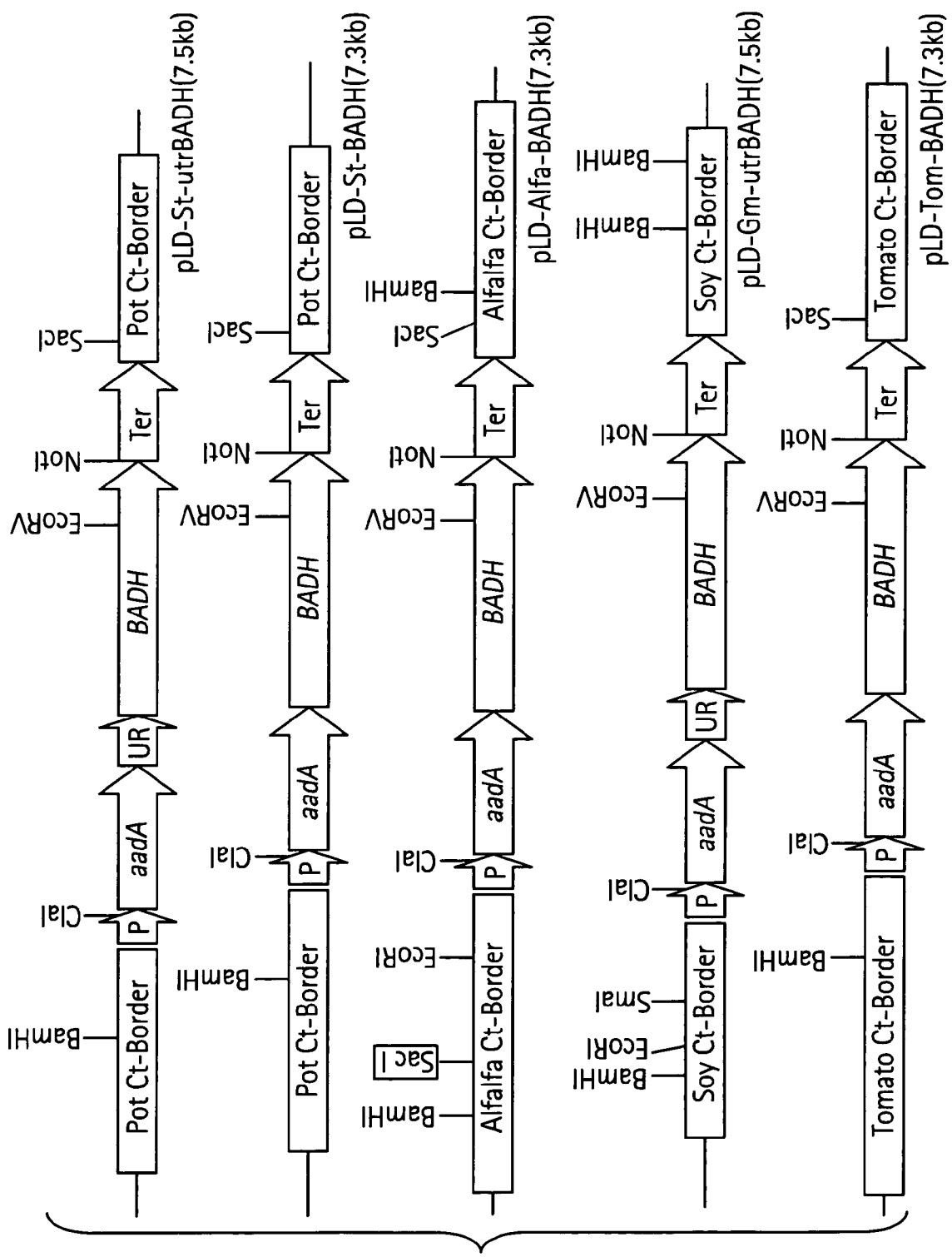

FIGS. 18A and 18B show other vectors suitable for operon expression.

DETAILED DESCRIPTION OF THE INVENTION

This invention is related to transformation of the plastid genome applicable to all plastids of plants. These include chromoplasts which are present in the fruits, vegetables and flowers; amyloplasts which are present in tubers like the potato; proplastids in roots; leucoplasts and etioplasts, both of which are present in non-green parts of plants.

The invention provides in one aspect a single vector or construct which encodes more than one heterologous protein product. The second aspect of the invention relates to the maximal production of heterologous protein by co-expressing it with another polypeptide or a chaperone that induces crystallization of said protein.

The first aspect of the invention provides that a heterologous DNA fragment that is introduced into a plastid vector (described below) encodes more than one gene. In one example, the DNA encodes an operon of three genes and produces proteins from three genes. This aspect of the invention to co-expressing multiple genes is beneficial if one desires to introduce a biosynthetic pathway into plants that comprises multiple steps. For example, a three step synthesis of a desired compound might require three different enzymes. Co-expressing all three enzymes in the chloroplast can be accomplished according to this invention. Thus, a single transformation will generate a recombinant plant possessing all three heterologous enzymes which can function in concert to produce the desired product.

The second aspect of the invention is that the yield of heterologous gene expression is greatly enhanced if the desired protein is in crystal form in the transformed plant, as provided by this invention. This is accomplished by co-expressing the desired gene with a second gene encoding a chaperone protein that directs crystallization. Data given in the specification shows almost 100 fold greater amounts of insecticidal protein can be found in plants co-expressing the chaperone protein versus plants having only the gene encoding the insecticidal protein. The expression cassette itself can be modified to include a selectable marker, a gene encoding the chaperone protein and any desired heterologous gene. Such applications will be beneficial for the high level production in plants of other desired protein products as well.

A further aspect of the invention describes a plant bioremediation system. A plant bioremediation system employing chloroplast transformants have a number of advantages. First, plants have the genetic capacity (using hundreds, even thousands, of genes) to extract at least 16 metal cation and oxyanion nutrients from the soil and ground water. This capacity can be chemically and genetically manipulated to extract environmental pollutants. Second, plants have extensive root systems to help in this mining effort; typical estimates are as high as $100 \times 10^6$ miles of roots per acre [Dittmer, H. J. (1937) Amer. J. Botany 24:417-420]. The root systems of various macrophytes can reach up to 40 feet into the soil. In addition, plants are photosynthetic and govern as much as 80% of the available energy at any given time in most ecosystems. Through photosystem I (a system not found in photosynthetic bacteria), they use light energy to generate large amounts of reducing power (as NADPH) that can be used to efficiently reduce metal ions. Plants photosynthetically fix $CO_2$ and reduce it to make their own carbon/energy source. This reduced carbon energy is used by plant roots to live heterotrophically. This redox power can also be used to reduce toxic metal ions like Hg(II) [Rugh et al. (1996) supra]. Many plants can produce large amounts of biomass annually with the potential both to enrich contaminated soil with carbon and nutrients and/or remove metal ions from the soil. The site of action of mercury within the chloroplasts, ability to express bacterial operon via the chloroplast genome, and several other environmental benefits of chloroplast genetic engineering make this an advantageous system for metal remediation.

An additional benefit of the metal resistant plants is their ability to harvest metals; precious and semi-precious metals can be reduced and thereby trapped in plant tissues. These metals include can include gold, silver, platinum, rhenium, copper, palladium, nickel, zinc and cadmium, where the corresponding metal ions are reduced by the metal resistance gene product in those plants.

In addition, this invention also introduces a novel approach for mercury and organomercurial bioremediation in water. Two organisms are used as model systems. One is *Synechocystis*, a photosynthetic bacterium (Cyanobacterium) that grows in salt and fresh water (in a high temperature range, from ice to hot springs). The other is *Chlorella vulgaris*, a green algae that grows in fresh water. These organisms are transformed with the merA and merB genes (mer operon) to remove mercury and organomercurials from water. Transformed cells could be applied for sludge treatment and in water treatment to remove organomercury and mercury form water and sediments before releasing them to the environment, especially from industrial effluents that generate byproducts with mercury.

"Metal resistance" means that a non-naturally occurring organism is not inhibited by the presence of at least one of divalent cations of mercury, cadmium, cobalt, trivalent cations of gold, and monovalent silver ion, at concentrations (levels) at which a naturally occurring (wild-type) counterpart of the non-naturally occurring organism is inhibited or exhibits symptoms of toxicity. It is not intended that the term metal resistance refer to resistance to unlimited concentration of metal ions, but rather the term is relative in that it relies on comparison to the properties of a parental strain.

A "metal resistance coding sequence" is one which encodes a protein capable of mediating resistance to at least one metal ion, including, but not limited to, divalent cations of mercury, nickel, cobalt, trivalent cations of gold, and by monovalent cations of silver. Also within the scope of this definition are mutant sequences which determine proteins capable of mediating resistance to divalent cations of lead, cadmium and copper.

An "organomercurial resistance coding sequence" is one whose protein product mediates resistance to such organic mercury compounds as alkylmercurials and certain aromatic mercurials, for example, mono- or dimethylmercury, typically in conjunction with a metal resistance gene such as merA. As specifically exemplified herein, the organomercurial resistance gene is the methylmercury lyase gene (merB) and its gene product confers resistance to organomercurial compounds such as methymercury, p-chloromercuribenzoate (PCMB) and p-hydroxymercuribenzoate in conjunction with the merA gene product (mercury ion reductase).

The metal resistance protein (MerA protein, mercuric ion reductase) is exemplified by that from Tn21, a bacterial mercury resistance transposon originally isolated from the IncFII plasmid NR1. In addition to reducing mercuric ions, the Tn21 MerA reduces trivalent gold and monovalent silver cations [Summers and Sugarman (1974) Journal of Bacteriology 119:242-249]. Monovalent silver and certain divalent metal cations have been shown to be competitive inhibitors of mercuric ion reduction in vitro [Rinderle et al. (1983) Biochemistry 22:869-876]. MerA mediates resistance to trivalent gold, divalent cobalt, divalent copper and divalent nickel cations as well as divalent ionic mercury.

It is understood that nucleic acid sequences from nucleotide 14 through nucleotide 1708, or MerApe 20, MerApe 29, MerApe 38 or MerApe 47 will function as coding sequences synonymous with the exemplified merApe9 coding sequence. Nucleic acid sequences are synonymous if the amino acid sequences encoded by those nucleic acid sequences are the same. The degeneracy of the genetic code is well known to the art; i.e., for many amino acids, there is more than one nucleotide triplet which serves as the codon for the amino acid; for expression in plant cells or tissue it is desired that codon usage reflect that of plant genes and that CpG dinucleotides be kept low in frequency in the coding sequence. It is also well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in Atlas of Protein Sequence and Structure, Vol. 5, Suppl. 3, pp. 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

The expression of merB in plants confers resistance to and/or the ability to detoxify organomercurials including, but not limited to, alkylmercury compounds wherein the alkyl group is either straight chain or branched, alkenyl mercury compounds, allyl mercury, alkynyl mercury compounds, aromatic mercury compounds, wherein there are from one to about 6 aromatic rings, and other organomercurials including but not limited to humic acid-containing mercury compounds. The MerB protein also mediates resistance to and/or detoxifies organo-metals including, but not limited to, organic lead, organic cadmium and organic arsenic compounds, where those organometals can be alkyl, aklenyl, alkynyl or aromatic metal compounds.

Coding sequences suitable for expression in a plant are operably linked downstream of a constitutive or a regulated promoter construct. Transgenic plants can be constructed by use of chloroplast universal vector containing a 5' a part of a chloroplast spacer sequence, a promoter that is operative in the chloroplast of the target plant cells, at least two heterologous DNA sequences encoding merA and merB, a gene that confers resistance to a selectable marker; a transcription termination region functional in the target plant cells; and a 3' part of the chloroplast spacer sequence. Alternatively, the vector may not contain a terminator.

The mer operon-expressing plants can be used in the remediation of mercury-contaminated soil to block the biomagnification of methyl mercury up the food chain. Deep-rooted trees like cottonwood and sweetgum, which inhabit bottom lands, can be transfomred to express mer A and merB. These species have roots that grow in the same general area of the sediment as sulfate-reducing bacteria. As the transgenic plant roots take up methyl mercury, MerB breaks the carbon mercury bond to produce Hg(II). Hg(II) is a highly reactive metal ion and should end up sequestered in plant tissues bound to various thiol groups.

Hg(II) produced from the MerB reaction and additional Hg(II) taken up from the environment through its normal mining of nutrients is reduced to Hg(0) by the MerA reaction. Hg(0) is released directly from the roots or transpired up the vascular system of the plant, as are waste gasses like $CO_2$ from some plants [Dacey, J. W. (1980) Science 210: 1017-1019; Dacey, J. W. (1981) Ecology 62:1137; Raven et al. (1986) In: Biology of Plants, Worth Publishers, N.Y., p. 775]. By lowering the total levels in the soil, less methyl mercury will be produced by sulfate-reducing bacteria. Using the MerA and MerB together in transgenic plants at contaminated sites lowers total Hg(II) levels and destroys environmental methyl mercury, thus preventing a large portion of the methyl mercury from moving through the environment.

The Hg(0) entering the environment joins the enormous and stable pool of Hg(0) in the atmosphere (Nriagu (1979) In: The Biogeochemistry of Mercury in the Environment, (New York: Elsevier) with half life of over one year. Because Hg(0) is not easily returned to earth, this pool is not thought to contribute less significantly to man made contamination of the environment. In contrast, atmospheric Hg(II) species (i.e., mercury released from coal burning or methyl mercury released naturally) are rapidly returned to earth by rain and dry deposition with a half-life of about 1-2 weeks. Thus, volatilization of relatively small amounts of Hg(0) with good air circulation effectively removes mercury from terrestrial and aquatic environments.

Once a transgenic plant population expressing MerA and MerB is established, these plants efficiently process mercury. Over the subsequent few decades these plants remove or detoxify most mercury from at a site. Relying only on currently available biological and chemical processing, the efflux rates of Hg(0) from mercury contaminated sites are extremely slow. At one such government site it is estimated that only 10 kg of the 80,000 kg present in the soil is released as Hg(0) per year (Lindberg et al. (1995) Environ. Sci. Tech. 29, 126-135). The levels of atmospheric mercury at this and most sites (4-10 ug/m.sup.3) are 10,000 fold below what the EPA/OSHA recommend as the maximimum allowable levels (U.S. Public Health Service (1994) Toxicological Profile for Mercury. In: Regulations and Advisories, U.S. Public Health Service, Washington, D.C., pp.261-269). Even if transgenic plants at this site increased the efflux rate of metallic mercury 200 times, the level of atmospheric mercury would still be 50 fold below these allowable levels. The transgenic plants of the present invention allow the efficient removal of toxic metal compounds such as methyl mercury and ionic mercury from soil, sediment, and aquatic environments, thus meeting a longfelt need for efficient bioremediation of metal and organometal contaminated sites.

The Operons of the Vector

The cry2Aa2 Operon. The preferred embodiment of the invention is the use of *Bacillus thuringiensis* (Bt) cry2Aa2 operon as a model system to demonstrate operon expression and crystal formation via the chloroplast genome of tobacco. This operon contains three open reading frames (ORFs). Cry2Aa2 is the distal gene of this operon. The ORF immediately upstream of cry2Aa2 codes for a putative chaperonin that facilitates the folding of cry2Aa2 (and other selected target proteins) to form proteolytically stable cuboidal crystals. Because CRY protein levels decrease in plant tissues late in the growing season or under physiological stress, a more stable protein expressed at high levels in the chloroplast throughout the growing season should increase toxicity of Bt transgenic plants to target insects and help eliminate the development of Bt resistance. The function of the third ORF is not yet known. The invention comprises the operon with the third gene and also with the operon without the third gene.

The mer Operon. Another embodiment of the invention uses the mer Operon. The genes for mercury resistance are known as Mer genes, they are found in operons of bacterial pasmids; different genes constitute operons, but the two most important are: the merA that codes for the mercuric ion reductase and the merB that codes for the organomercurial lyases (Foster, 1983; Summers et al. 1978, 1986). Mer A is a 1.7 kb gene that needs NADPH as a co-factor to reduce mercury to a volatile, non-reactive and less toxic form of mercury (Hg0) (Begley et al. 1986). Mer B is a 638 bp gene that undergoes the protonolysis of organomercurials by removing the organic group and releasing elemental mercury, which is detoxified by merA (Jackson et al. 1982). A polycistron containing both genes allows effective degradation of mercury and organornercurials.

Alternative Operons

Other Cry or Cyt operons may be used in this invention. Any operon which comprises at least one of the 133 genes shown in the article MMBR, September 1998, pages 805-873, Vol 62, No. 4, Revision of the Nomenclature for the BT Insecticidal Crystal Proteins by Crickmon et al., the genes of which codes for the corresponding BT protein; and the chaperonin which facilitates protein folding can be used. Likewise, any operon which comprises at least one of the toxins enumerated in Table 15.1 or at least one of the of Molecular Biotechnology by Glick and Pasternak can be used. Similarly, any operon which comprises a gene which codes for a delta-endotoxin and the chaperonin which facilitates protein folding can be used. In addition, any operon which comprises at least a plasmid identified in Table 13.1 of the of Molecular Biotechnology by Glick and Pasternak can be used.

The Chaperonins

Chaperonins are a class of a protein referred to as chaperones which has been shown to consist of helper proteins in chain folding and assembly with the cells (Gierasch and King, 1990). They facilitate the folding and assembly of newly synthesized polypeptide chains into functional three-dimensional structures by preventing off-pathway reactions during folding that lead to aggregation (Agashe V R et. al. 2000). Chaperonins provide a sequestered environment in which folding can proceed unimpaired by intermolecular interactions between non-native polypeptides (Agashe V R et. al. 2000). Those skilled in the art will be familiar with the *E. Coli* chaperonins: groEL and groES (Viitanen P V et. al.

1995), (Gierasch and King, 1990). Plant chaperonins chaperonin-60 and chaperonin-10, which are homologous of gro-EL and gro-ES, respectively. Homologous of the *E. Coli* groEL and groES continue to be identified. For instance, a stable complex of the chaperonins has been isolated and crystallized from the extremely thermophilic bacterium *Thermus thermophilus* (Lissin N M et. al. 1992). Likewise, plant chaperonins—located both in plastids and the cytosol, continue to be identified (Baneyx F. et. al., 1995; Viitanen P V et. al., 1995; Burt W J et. al. 1994, Grellet F. et. al. 1993; Bertsch U et. al., 1992). These articles are hereby incorporated in their entirety by reference.

Figure 1A:
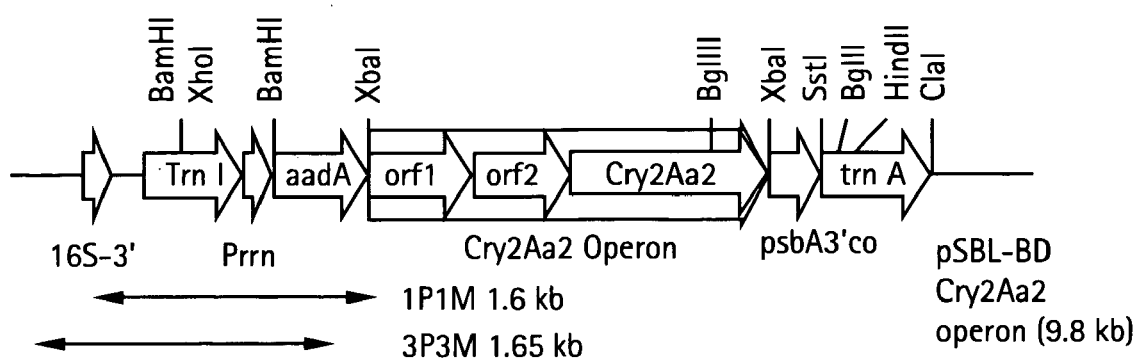
Figure 1B:
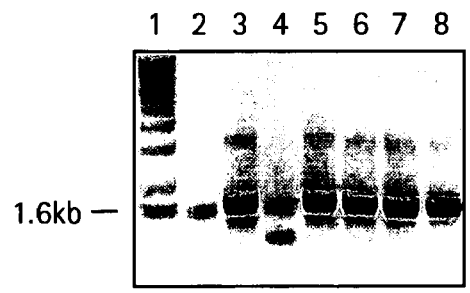
Figure 1C:
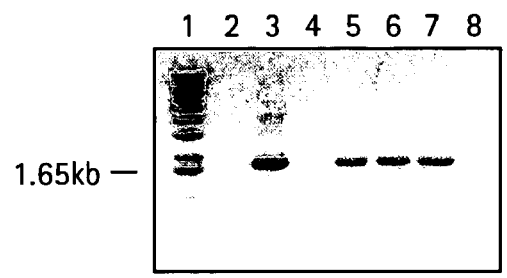
Figure 2C:
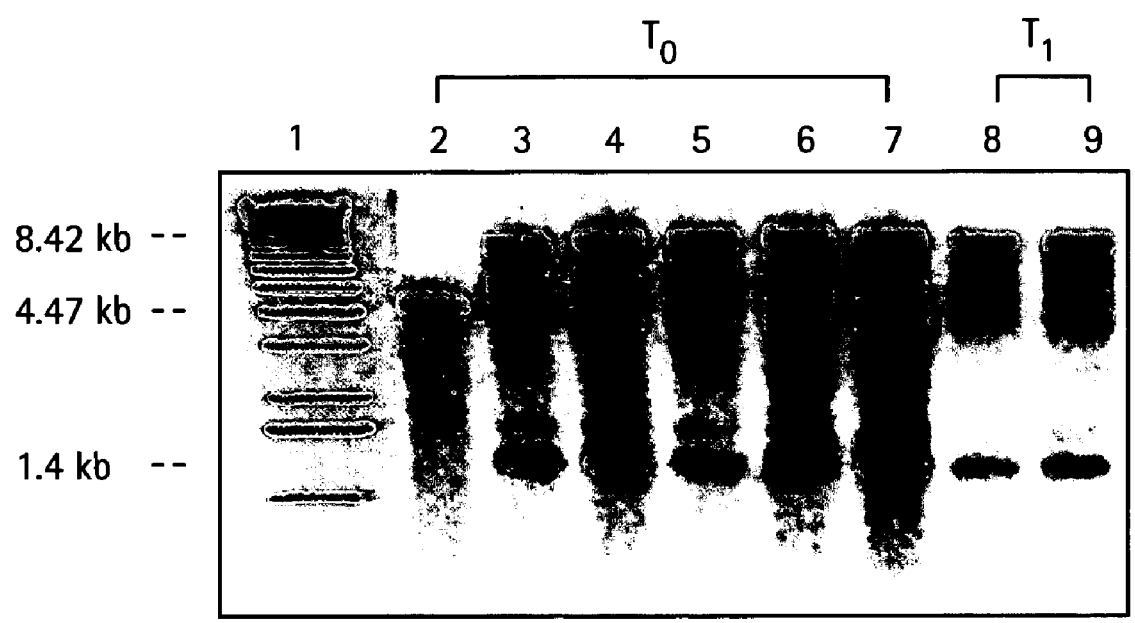
Figure 3:
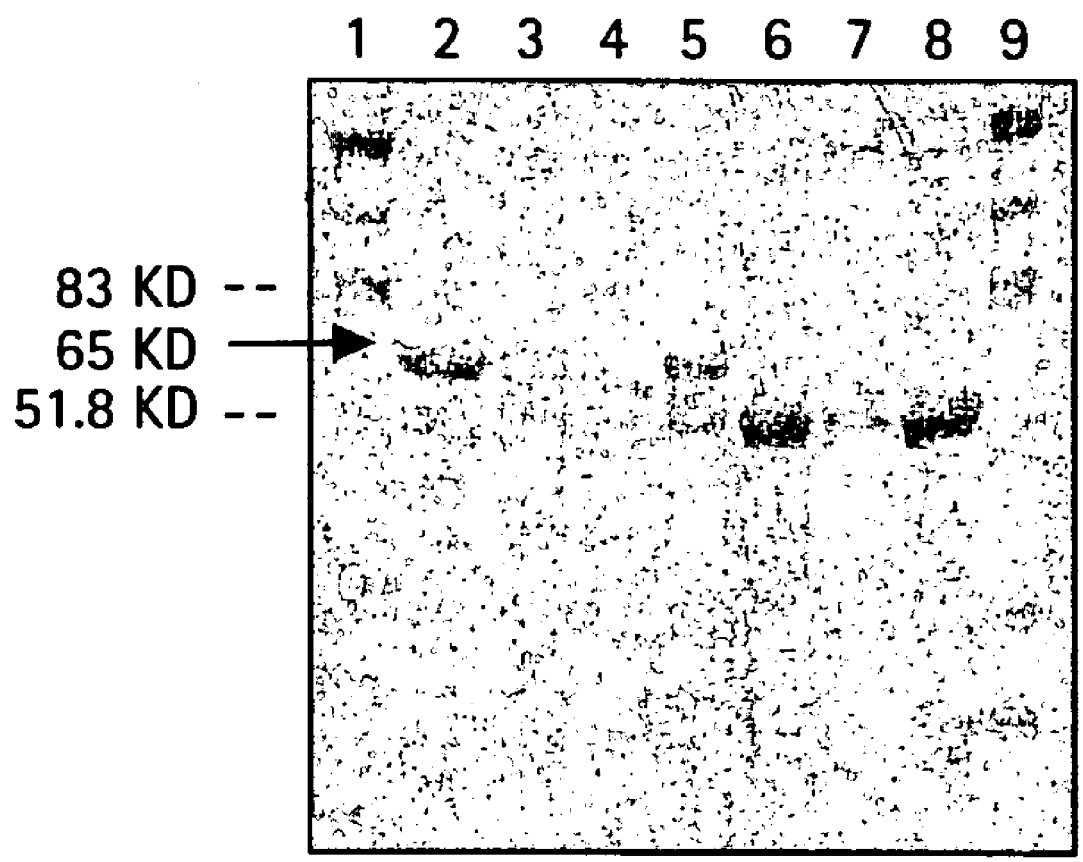
Figure 4A:
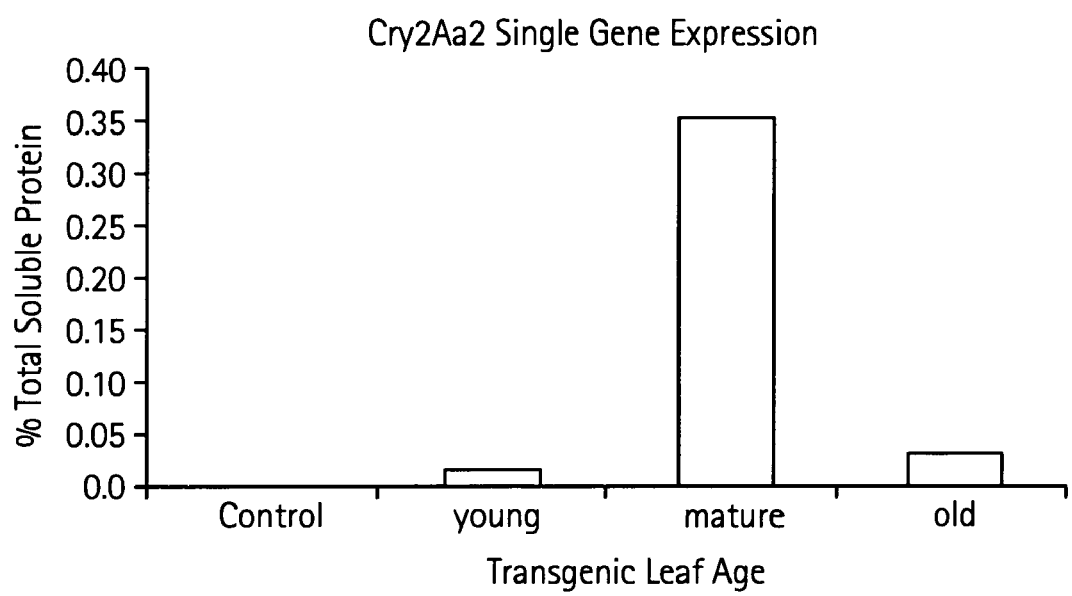
Figure 4B:
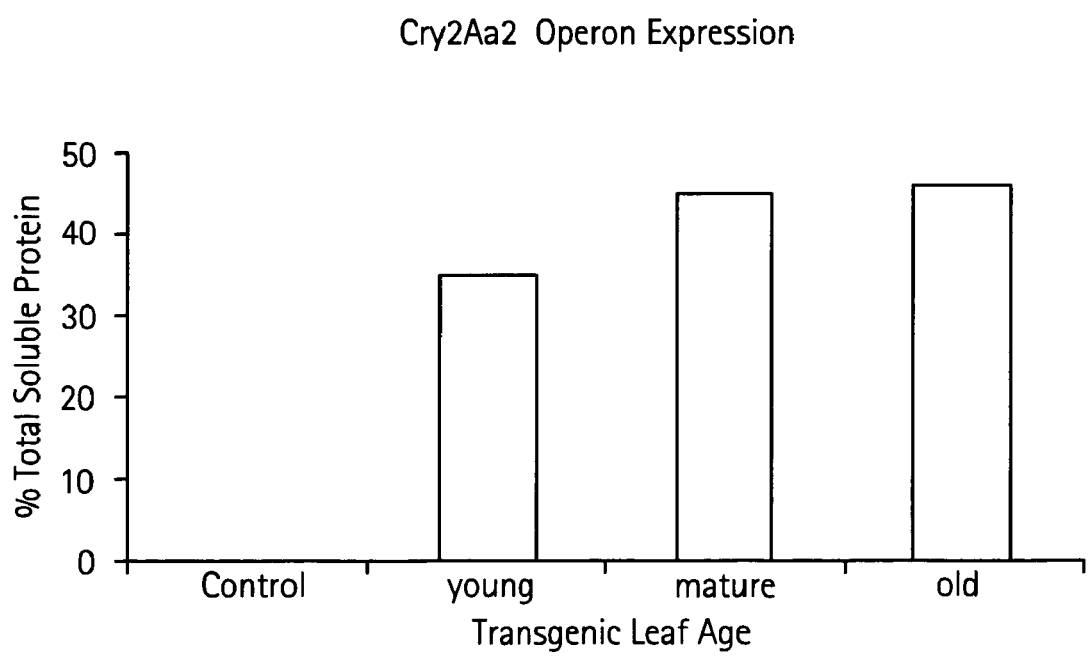
Figure 5A:
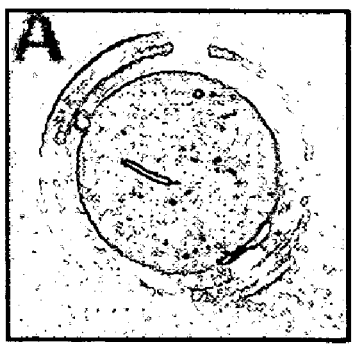
Figure 5B:
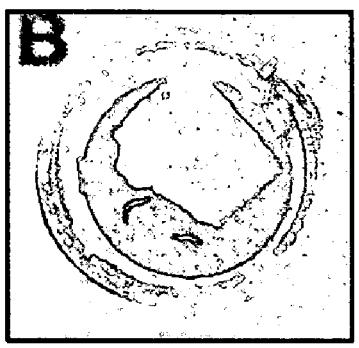
Figure 5C:
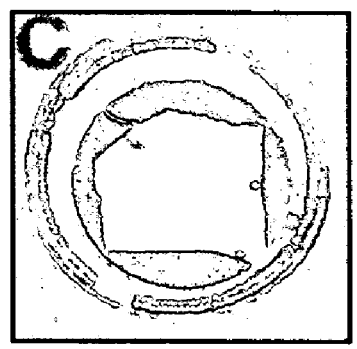
Figure 5D:
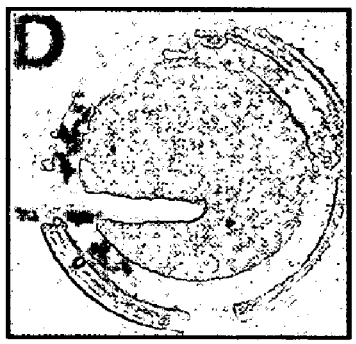
Figure 5E:
Figure 5F:
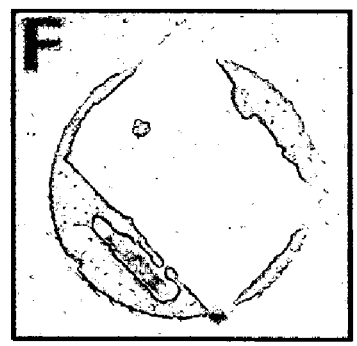
Figure 5G:
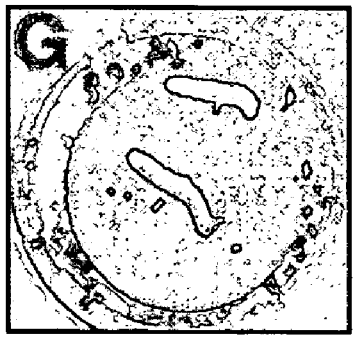
Figure 5H:
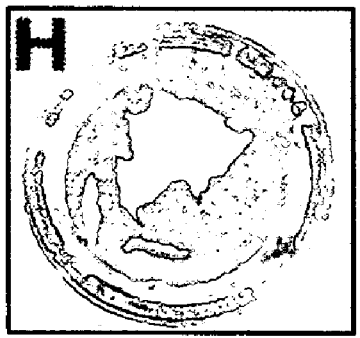
Figure 5I:
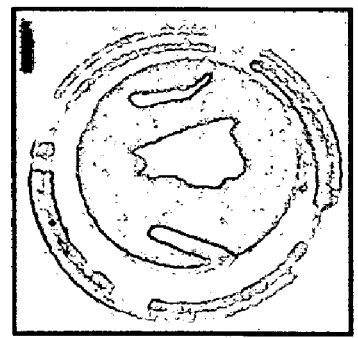
Figure 6A:
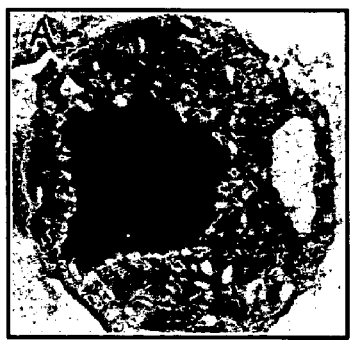
FIG. 6A shows the electron micrographs of operon derived Cry2Aa2 leaf sections in a young leaf.
Figure 6B:
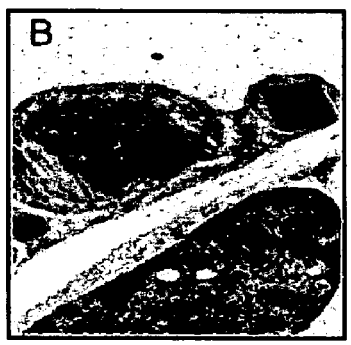
FIGS. 6B and 6D show the electron micrographs of operon derived Cry2Aa2 leaf sections in mature leaves.
Figure 6C:
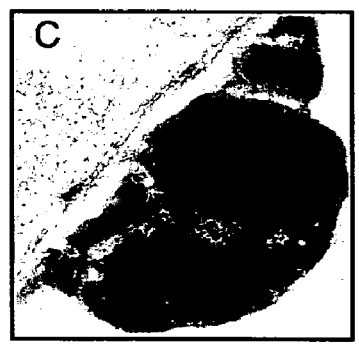
FIG. 6C shows the electron micrograph of operon derived cry2Aa2 leaf sections in an old, bleached leaf (C).
Figure 6D:
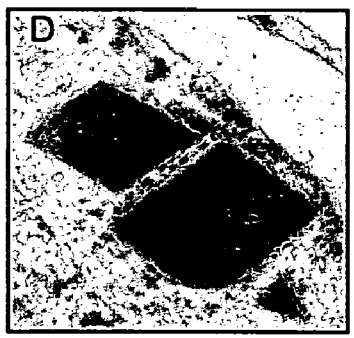
Figure 6E:
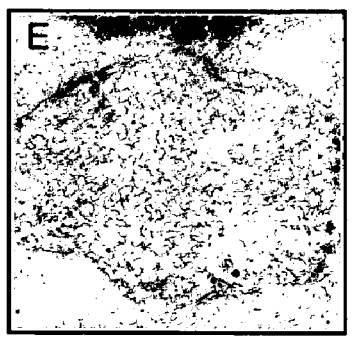
FIG. 6E shows the electron micrographs of Operon Derived Cry2Aa2 leaf sections in a single Gene derived Cry2Aa2 mature leaf.
Figure 6F:
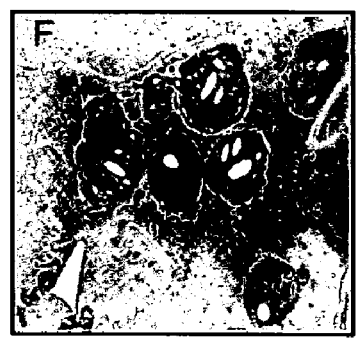
FIG. 6F shows the electron micrographs of Operon Derived Cry2Aa2 leaf sections in a mature untransformed leaf (F).
Figure 7:
FIG. 7 shows the phenotypes of untransformed (A) or transformed with the cry2Aa2 gene (B) or cry2Aa2 operon (C).
Figure 8:
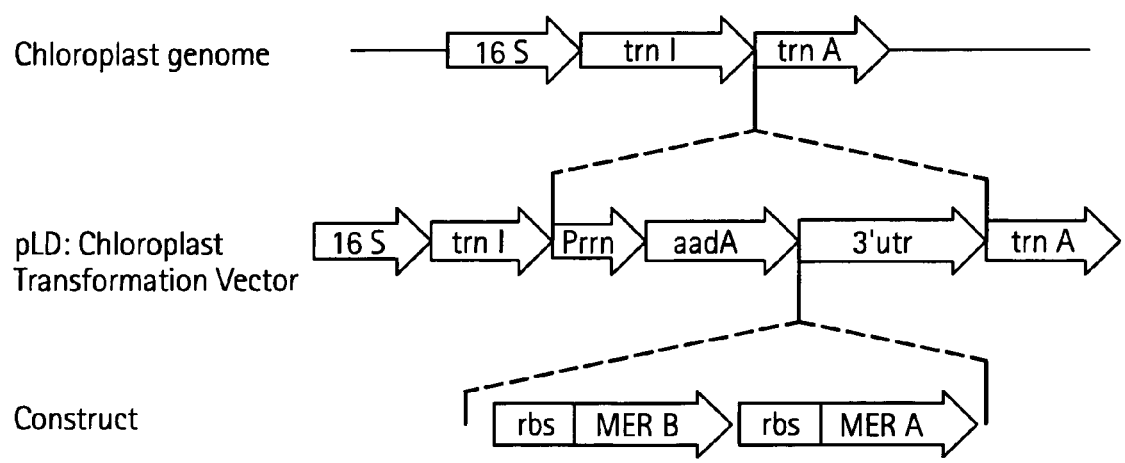
FIG. 8 shows a pLD-merAB chloroplast vector.

The preferred embodiment of this invention use of those bacterial chaperonins that are capable of facilitating the crystallization of the Bt endotoxin polypeptides by means of the UV Ct vector and in the transformed plants.

The Vectors

This invention contemplates the use of vectors which are capable of stably transforming the chloroplast genome. Such vectors include chloroplast expression vectors such as pUC, pBlueScript, pGEM, and all others identified by Daniell in U.S. Pat. No. 5,693,507 and 5,932,479. These publications and patents are herein incorporated by reference to the same extent as if each individual publication or patent was specifically and individually indicated to be incorporated by reference.

Universal Vector. A preferred embodiment of this invention utilizes a universal integration and expression vector competent for stably transforming the chloroplast genome of different plant species (Universal Vector). The universal vector and its construction have been described by the earlier Publication No. WO99/10513, International publication date: 4 Mar. 1990, which is herein incorporated in its entirety.

The 4.0 kb cry2Aa2 operon was inserted into the universal chloroplast expression vector pLD CtV2 (5.8 kb) to form the final *E. coli* and tobacco shuttle vector pLD-BD Cry2Aa2 operon (9.8 kb) (FIG. 1A). This vector could be used to transform chloroplast genomes of several plant species because the flanking sequences are highly conserved among higher plants. This vector contains the 16S rRNA promoter (Prrn) driving the aada gene (aminoglycoside 3'-adenylyltransferase) for spectinomycin selection and the three genes of the cry2Aa2 operon. The terminator is the psbA 3' region from the tobacco chloroplast genome from a gene coding for the photosystem II reaction center component. The 16S rRNA promoter is one of the strong chloroplast promoters recognized by both nuclear and plastid encoded RNA polymerases in tobacco and the psbA 3' region stabilizes the transcript of foreign genes. This construct integrates both genes into the spacer region between the chloroplast transfer RNA genes coding for isoleucine and alanine within the inverted repeat (IR) region of the chloroplast genome by homologous recombination. The integration into these transcribed spacer regions allow the gene to be inserted without interfering with gene coding regions. Also, each genome will contain two gene copies due to integration into the two inverted repeat regions resulting in a higher copy number (7,000-8,000 copies per cell) and higher levels of expression. However, the two genes may also be integrated outside of the IR region resulting in a lower copy number. Chloroplast transgenic plants were obtained as described previously by Daniell (1993, 1997).

Mer operon vectors with and without terminator: In order to understand the role of 3'UTRs in chloroplast foreign gene expression (in mRNA stability and transcription termination), chloroplast vectors with and without 3' UTRs were made. The PCR products, merA and merB were cloned independently into the pCR2.1 vector (In Vitrogen). Then, the orientation of the merB gene integration was checked. Once the correct orientation was found, the vector TA-merB was cut with a ClaI/EcoRV. MerA was cut with ClaI and EcoRV, and the fragment (merA) was isolated by gel electrophoresis. Then, the merB and merA genes were ligated. After the ligation, both genes (merB and merA) in-frame were ready for insertion into the pLD vector. After cutting pLD vector with PstI to linearize the vector and to remove the terminator, the merB-merA cassette extracted from the TA-vector was ligated into the pLD vector (FIG. 8). The final step was to check for correct orientation. Thus the pLD-merAB vector lacking 3' UTR was constructed.

To make the pLD-merA.B-3'UTR, specific set of primers were used to amplify the whole cassette from the TA-merAB vector. The 5' primer was designed with an EcoRV site and the 3' primer with a XbaI site. These restriction sites allowed the integration into the pLD vector only in the right orientation.

Chloroplast Integration of Foreign Genes

Foreign gene integration into the chloroplast genome was determined by PCR screening of chloroplast transformants (FIGS. 1A,B,C). Primers were designed to eliminate spectinomycin mutants and nuclear integration. The first primer set, 1P1M, lands one primer (1P) on the 3' end of the 16s rRNA flanking sequence and another primer (1M) on aadA (FIG. 1A). This is to distinguish between spectinomycin mutants and true spectinomycin transformants. A 1.6 kb fragment is seen in true transformants (FIG. 1B, lanes 3,5,6,7). Lane 4 shows a spectinomycin mutant with no PCR product.

Untransformed tobacco DNA (lane 2) expectedly shows no product, while pLD-BD cry2Aa2 operon plasmid DNA in lane 8 produced the 1.6 kb fragment. The second primer set, 3P3M, lands one primer (3P) on the native chloroplast genome adjacent to the point of integration, and another primer (3M) on the aadA gene (FIG. 1A). This primer set generated a 1.65 kb PCR product in chloroplast transformants (FIG. 1C, lanes 3,5,6,7). Untransformed tobacco DNA (lane 2) showed no PCR product, and pLD-BD. cry2Aa2 operon plasmid DNA in lane 8 also showed no PCR product because 3P lands on native chloroplast DNA. Lane 4 was negative for chloroplast integration and again proving this transformant to be a spectinomycin mutant.

Southern blot analysis was done to further demonstrate site-specific chloroplast integration of the 4.0 kb cry2Aa2 operon and to determine heteroplasmy or homoplasmy (FIG. 2). Bglll digested DNA from transformed plants produce 8.42 kb and 1.4 kb fragments (FIG. 2B) when probed with the 0.81 kb probe (FIG. 2A) that hybridizes to the trn1 and trnA flanking sequences. Transgenic plant DNA ($T_0$ and $T_1$) produced the 8.42 kb and 1.4 kb fragments (FIG. 2C, lanes 3-9). A 4.47 kb fragment (FIG. 2A) is seen in untransformed plant DNA (FIG. 2C lane 2). To plant DNA also shows this native untransformed 4.47 kb fragment (FIG. 2C, lanes 3-7), thereby showing heteroplasmy in the $T_0$ generation. This 4.47 kb native band is absent from the $T_1$ generation (FIG. 2C, lanes 8-9), thus indicating homoplasmy. If only a fraction of the genomes were transformed, the gene copy number should be less than 8,000 per cell. Confirmation of homoplasmy in $T_1$ transgenic lines indicates that the Cry2Aa2 operon gene copy number could be as many as 7000-8,000 per cell.

CRY2Aa2 protein expression and quantification: Expression profile of the operon derived (OD) Cry2Aa2 and single gene derived (SG) Cry2Aa21 is shown on a Coomassie stained SDS-PAGE gel (FIG. 3). The primary goal of this experiment is to investigate the location of the operon derived Cry2Aa2 protein (the pellet or supernatant) and correlate with cuboidal crystals observed in electron micrographs (see FIG. 6). Lane 2 contains partially purified 65 KD Cry2Aa2 from *E. coli*. Because crystalline Cry2Aa2 inclusion bodies are solubilized at high alkaline pH, the 50 mM NaOH solubilized pellet was analyzed from each plant sample after centrifugation for 20 min at 13,000 g (lanes 3, 5, 7). Results show that OD Cry2Aa2 expression forms crystalline inclusion bodies because the protein is found mostly in the pellet after centrifugation (lanes 5-6). In contrast, expression of SG Cry2Aa2 is observed in both the pellet and the supernatant (lanes 3-4). No Cry2Aa2 expression was seen in untransformed tobacco in either the supernatant or the pellet (lanes 7, 8).

Cry 2Aa2 polypeptides (FIG. 3, lanes 3, 5) were scanned using Storm 840 Gel Scanner and Image Quant Software (Molecular Dynamics). The operon-derived expression results only in a 2.5 fold more accumulation of Cry2Aa2 than that of single gene derived cry2Aa2 in the pellet fraction; this does not correlate with more than 100 fold difference observed in ELISA (FIG. 4). The reason for this discrepancy is the extreme difference in solubilization between SG Cry2Aa2 derived amorphous inclusion bodies and the OD Cry2Aa2 derived cuboidal crystals, as reported previously.

Despite the large difference in protein accumulation (as shown by ELISA and electron micrographs, FIGS. 4, 6), the concentration of solubilized protein loaded in the pellet fraction was similar in SG Cry2Aa2 and OD Cry2Aa2 (FIG. 3, lanes 3, 5). Attempts to completely solubilize crystalline inclusion bodies for SDS PAGE analysis were not successful because higher pH interfered with gel electrophoresis and repeated dilution decreased protein concentration below detectable levels in Coornassie stained gels.

However, for quantification using ELISA it was possible to completely solubilize crystalline inclusion bodies under optimal conditions and dilute the protein to fit within the linear range of the Cry2aA2 standard. Therefore, protein expression levels of SG Cry2Aa2 and OD Cry2Aa2 were quantified using ELISA (FIG. 4). Additionally, CRY protein accumulation in young, mature, and old transgenic leaves derived from a single gene or operon was compared to investigate their stability over time. Young, mature, and old leaves expressed SG Cry2Aa2 at 0.014%, 0.36%, and 0.03% respectively (FIG. 4A). Cry2Aa2 levels peaked in the mature leaf (0.36%) and drastically declined to 0.03% as the plant senesced. However, young, mature, and old leaves containing OD Cry2Aa2 accumulated at 34.9%, 45.3%, and 46.1% respectively (FIG. 413). As these transgenic plants aged, OD Cry2Aa2 concentrations remained stable and did not decline like the SG Cry2Aa2. The presence of the operon-expressed putative chaperonin should enable the toxin to be folded into stable crystalline structures that are protected from degradation. Based on quantitative expression, the cry2Aa2 operon derived expression levels are comparable to that of the RuBis Co, the most abundant protein on earth that compromises up to 65% of leaf soluble protein.

Insect Bioassays: Five-day-old tobacco budworm (*Heliothis virescens*), ten day old cotton bollworm (*Helicoverpa zea*) and beet armyworm (*Spodoptera exigua*) larvae consumed the entire leaf after 24 hrs on the untransformed control (FIGS. 5A, D, G). *H. virescens* feeding on SG Cry2Aa2 leaves died after 5 days (FIG. 5B) while insects died after 3 days on OD Cry2Aa2 leaves (FIG. 5C). For SG Cry2Aa2, *H. zea* consumed considerable leaf material after 24 hr, stopped feeding after three days and died after five days (FIG. 5E). *H. zea* consumed very little OD Cry2Aa2 material after 24 hours, stopped feeding, and died after five days (FIG. 5F). *S. exigua* feeding on SG Cry2Aa2 (FIG. 5H) or OD Cry2Aa2 (FIG. 51) were lethargic after 24 hours and died after 48 hours. Milkweed leaves dusted with OD Cry2A2 transgenic pollen were not toxic to Monarch butterfly larvae (data not shown) confirming earlier observations that foreign proteins are not present in tobacco pollen.

Electron Microscopic Analysis: Untransformed and transgenic leaf sections were immunogold-labeled with a Cry2A polyclonal antibody (FIG. 6). FIGS. A-C show developmental OD Cry2Aa2 in chloroplasts in young, mature, and old leaves, respectively. In a young green OD Cry2Aa2 transgenic leaf (FIG. 6A), labeled Cry2Aa2 occupies a significant amount of the chloroplast, but no crystalline structures are observed. In a mature green OD Cry2Aa2 transgenic leaf (FIG. 6B), labeled Cry2Aa2 occupies a larger amount of the chloroplast than the younger leaf, resulting in crystals. Theses cuboidal crystals are essentially identical to those expressed in wild-type Cry2Aa2 crystals, or recombinantly in Bt or *E coli*. In an old bleached OD Cry2Aa2 transgenic leaf (FIG. 6C), labeled Cry2Aa2 maintains the crystalline structure and occupies the highest volume of the chloroplast observed, despite being bleached and senescent. These findings correlate with OD Cry2Aa2 ELISA results. In young developing leaves, OD Cry2Aa2 begins accumulation (34.9%), folds Cry2Aa2 into a cuboidal configuration in mature leaves occupying more cell volume (45.3%), and maintains this cuboidal structure and volume in old leaves (46.1%). Essentially, as the transgenic OD Cry2Aa2 plant ages, OD Cry2Aa2 is accumulated, folded and maintained.

FIG. 6D is a mature green OD Cry2Aa2 transgenic leaf showing crystal formation with no immunogold label. This probably occurs because as the Cry2Aa2 is folded by the putative chaperonin, epitopes are concealed thereby decreasing labeling. Crystal formation in FIG. 6D would cause the OD Cry2Aa2 to pellet after centrifugation as seen in SDS-PAGE FIG. 3 (lane 5). In EM analysis of mature leaves expressing SG Cry2Aa2 (FIG. 6E), protein aggregation is observed, although no crystalline folding is seen. Cry2Aa2 immunogold labeling occurs in an area of much lower density than is seen in OD Cry2Aa2 transgenic plants suggesting lower expression. These results also correlate with ELISA (0.36% in SG Cry2Aa2 in mature leaves). There is no localized antibody observed in untransformed tobacco (FIG. 6F).

Transgenic phenotypes: Phenotypes of OD Cry2Aa2 transgenic plants are not morphologically different from SG Cry2Aa2 transgenic plants (FIG. 7). Therefore, higher levels of expression and accumulation of CRY proteins did not visibly impact their phenotype. Both transgenic plants flowered and set seeds. Characterization of OD Cry2Aa2 $T_1$ transgenic plants for stable integration and transmission of foreign genes has been shown earlier (FIG. 2).

Possibility of Gene Pyramiding

This invention enables expression of polycistrons in the chloroplast genome. In contrast to prior efforts in engineering gene expression in transgenic plants, the present invention allows for this achievement in a single transformation event that is environmentally safe. The invention thus opens the possibility for gene pyramiding: the insertion of multiple insecticidal genes. The invention contemplates operons which include not only *Bacillus thuingiensis* (B.t.) insecticidal toxin genes, but also non-B.t. insecticidal toxin genes such as cholesteral oxidase, alpha-amylase inhibitors, protease inhibitors, the cowpea trypsin inhibitors, and the potato proteinase inhibitor II. Inclusion of multiple heterologous insecticidal toxin genes retards the ability of insects to develop resistance to bio-pesticides.

Expression of Biological Pathways

Further, this invention provides a method of engineering biological pathways into the chloroplast genome in a single transformation event that is environmentally safe. Because gene expression is controlled by one promoter, DNA sequences encoding the different genes necessary in a pathway can be co-expressed to the same levels. Once expressed, the genes of the pathway can act in concert. Gene expression can result in synthesis of enzymes that confer desired traits such as degradation of metal ions, herbicides, pesticides, solvents, toulene, napthalene, and other xenobiotics. An example is the chloroplast transformation of plant chloroplasts with the Mer operon leading to the biodegradation of mercury and organomercurials. Other pathways include the pigment biosynthesis pathway, biosynthetic pathways for enzymes that are could confer desired traits such as degradation of xenobiotic compounds noted above, pathways for amino acids such as the lysine biosynthetic pathway, and pathways for the synthesis of vitamins, carbohydrates, fatty acids, biopolymers and polyesters. Further examples are provided in chapters 12 and 13 of Molecular Biotechnology by Glick and Pasternak, which is herein incorporated by reference. Other xenobiotics which can be degraded using the system of this invention include those given in U.S. Pat. No. 4,259,444 to Chakrabarty which is herein incorporated by reference.

Expression of pathways can result in the production of compounds such as amino acids, fatty acids, carbohydrates, polymers, vitamins, antibiotics and dyes.

Efficient Expression of Bio-pharmaceuticals

The ability to express polycistrons also opens up the possibility of efficiently expressing bio-pharmaceuticals such as monoclonal antibodies. Those skilled in the art will know the four DNA sequences encoding proteins necessary to compose the molecule. Those skilled in the art will also know that these proteins should be produced in equal amounts (the same stoichiometric ratio). The PCT application entitled "Production of Antibodies in Transgenic Plastids," filed on Feb. 28, 2001 by Daniell, is hereby incorporated by reference to offer examples of such proteins. This invention allows for the coordinated expression of these sequences because they are driven by the same promoter. This method avoids the problems of the prior art; namely the pitfalls of nuclear transformation such as the positional effect and gene silencing.

Application to Other Plants.

This invention provides any higher plants, such as monocotyledonous and dicotyledonous plant species. The plants that maybe transformed via the universal vector with an antibiotic selectable marker may be solanacious plants or plants that grow underground. Most importantly, this invention is applicable to the major economically important crops such as maize, rice, soybean, wheat, and cotton. A non-exclusive list of examples of higher plants which may be so transformed include cereals such as barley, corn, oat, rice, and wheat; melons such as cucumber, muskmelon, and watermelon; legumes such as bean, cowpea, pea, peanut; oil crops such as canola and soybean; solanaceous plants such as tobacco; tuber crops such as potato and sweet potato; and vegetables like tomato, pepper and radish; fruits such as pear, grape, peach, plum, banana, apple and strawberry; fiber crops like the *Gossypium* genus such as cotton, flax and hemp; and other plants such as beet, cotton, coffee, radish, commercial flowing plants, such as carnation and roses; grasses, such as sugar cane or turfgrass; evergreen trees such as fir, spruce, and pine, and deciduous trees, such as maple and oak.

The invention now being generally described, it will be more readily understood by reference to the following examples which are included for purposes of illustration only and are not intended to limit the present invention.

In the experimental disclosure which follows, all temperatures are given in degrees centigrade (.degree), weight are given in grams (g), milligram (mg) or micrograms (.mu.g), concentrations are given as molar (M), millimolar (mM) or micromolar (.mu.M) and all volumes are given in liters (1), milliliters (ml) or microliters (.mu.l), unless otherwise indicated.

The invention is exemplified in the following non-limiting examples which are only for illustrative purposes and are not intended to limit the scope of the invention.

EXAMPLE 1

Bombardment and selection of transgenic plants: Tobacco plants were grown aseptically under fluorescent lights in the laboratory. Seeds were germinated on MSO medium at 27° C. with photoperiods of 16 hour light and 8 hour dark. Microcarriers coated with pLD-BD Cry2Aa2 operon DNA was used to bombard sterile leaves using the Bio-Rad PDS-1000/He biolistic device as described by Daniell (1997). Bombarded leaves were subjected to two rounds of selection on RMOP medium containing 500 µg/ml of spectinomycin to regenerate transformants.

PCR Analysis: DNA was extracted from leaves using the QIAGEN DNeasy Plant Mini Kit. PCR was done using the Perkin Elmer Gene Amp PCR System 2400. All PCR reactions were performed using the Qiagen Taq DNA Polymerase Kit. Primer sequences used were: 1P (5'-ACAATG-TAGCCGTACTGGA AGGTGCG GGTG-3') (SEQ ID NO: 1), 1M (5'-CGCGCTT AGC TGGATAACGCCACGGAA-3') (SEQ ID NO:2), 3P (5'-AAAA CCCGTCCTCA GTTCG-GATTGC-3') (SEQ ID NO: 3), and 3M (5'-CCGCGT-TGTTTCATCAA GCCTTACG-3') (SEQ ID NO: 4). Samples were run for 30 cycles with the following sequence: 94° C. for 1 minute, 70° C. for 1.5 minutes and 72° C. for 3 minutes. PCR product separated on 0.8% agarose gels.

Southern Blot Analysis: DNA from transformed and untransformed plants was digested with BglII and transferred to a nylon membrane by capillary action. The 0.81 kb probe was generated by digesting pLD-CtV2 vector DNA with BamHl/BglII and labeled with $^{32}P$ using the ProbeQuant™ G-50 Micro Columns (Amersham). Labeled probe was hybridized with the nylon membrane using the Stratagene QUICK-HYB hybridization solution and protocol.

SDS-PAGE Analysis: Transgenic and untransformed leaf material (600 mg) was ground to a powder in liquid nitrogen. Protein extraction buffer from the Cry2Aa2 plate kit from Envirologix (Portland, Me.) used for quantification was added to the powder and further grinding was performed. The mixture was centrifuged at 4° C. at 13,000 g for 20 minutes. The supernatant was removed, boiled in sample buffer, and loaded on a 10% SDS-PAGE gel. The pellet was resuspended in 50 mM NaOH and centrifuged at 4° C. at 5000 g for 5 minutes to pellet cell debris. The supernatant was removed, boiled in sample buffer, and loaded on a 10%

SDS-PAGE gel at 200V for 4 hours. Gels were stained for 2 hours with R-250 Coomassie Blue and destained overnight in 40% methanol and 10% acetic acid. The DC protein assay by Bio-Rad was used to determine total soluble and pellet protein concentration as followed by protocol.

ELISA: A Cry2Aa2 plate kit from Envirologix was used. Leaves expressing the SG Cry2Aa2, the OD Cry2Aa2, and untransformed tobacco were quantified and compared. Approximately 20 mg of leaf was ground in 100 μl of 50 mM NaOH to solubilize CRY proteins. Transgenic leaf extracts were diluted to fit in the linear range of the provided Cry2aA2 standard. The liquant microtiter plate reader from Bio-Tek read the plate at 450 nanometers (nm). A 1 ppm Cry2Aa2 standard was supplied by the kit and was used in the linear range between 200-1000 ng for quantification. Color development is proportional to Cry2Aa2 concentration in the sample extract. The DC protein assay by Bio-Rad was used to determine total soluble protein concentration as followed by protocol.

Insect Bioassays: Leaf disc bioassays were conducted on ca. 2 cm² excised leaf material, and placed on distilled water-soaked cardboard lids in 50×12 mm plastic petri dishes. Insects used were susceptible *H. virescens* (YDK) obtained from Fred Gould, North Carolina State University, *H. zea* obtained from the USDA AIRS facility in Tifton, G A and *S. exigua* from the lab of William Moar. Insects were tested as five day or ten day old. All larvae were reared on typical lepidopteran artificial diet prior to use. Two insects were assayed per leaf sample, except *H. zea* in which only 1 insect was added per leaf sample due to the cannibalistic nature of the insect (2 leaf samples for *H. zea*). All leaf samples for each replicate were from the same leaf. Two samples were evaluated per treatment, and observed daily for mortality and leaf damage for 5 days. Treatments were replicated three times.

Transmission Electron Microscopy and Immunogold Labeling: Immunogold labeled electron microscopy was performed as described by A. J. Vrekleij et. al. Sections were first incubated with 0.05M glycine in PBS buffer (10 mM phosphate buffer, 150 mM NaCl pH 7.4) for 15 minutes to inactivate residual aldehyde groups. The grids were then blocked by placing them onto drops of PBS with 5% BSA and 0.1% CWFS gelatin supplemented with 5% normal serum for 30 minutes, washed on drops of incubation buffer 3 times for 5 min each, and then incubated for 45 min with the polyclonal Cry2Aa2 to detect tobacco expression (diluted 1:10,000 in incubation buffer). To remove unbound primary antibody, sections were washed on drops of incubation buffer 6×5 min each. Sections were then incubated for 2 hours with a goat anti-rabbit IgG secondary antibody conjugate to 10 nm gold diluted 1:100 in incubation buffer. Sections were subsequently washed 6×5 minutes in incubation buffer, 3×5 min with PBS, and post-fixed in 2% glutaraldehyde diluted in PBS for 5 min. Following post-fixation, sections were washed in PBS 3×5 minutes, in distilled water 5×2 min each, and post-stained using uranylacetate and lead citrate. Sections were then examined in a Zeiss EM 10 transmission electron microscope at 60 kv.

EXAMPLE 2

*E. Coli* Transformants. Due to the similarity of protein synthetic machinery (Brixey et al. 1997), expression of all metal resistance conferring chloroplast vectors are first tested in *E. coli* before their use in tobacco transformation. The activity of the enzymes, mercury ion reductase (merA) and organornercurial lyase (merB) are tested by transforming *E. coli* (XLI-blue) with the recombinant plasmids and growing them in LB solid medium with $HgCl_2$ (FIG. 9). The cells, control (XLI-bue), pLD-merAB and pLDmerAB-3'UTR are grown in different concentrations of Hg $Cl_2$. Control cells do not grow even at concentrations less than 25 μM Hg $Cl_2$ but the transformed cells grow well even at 100 μM $HgCl_2$-(FIG. 10). The ability to grow at these high concentrations of mercury in which control is not able to grow, confirms the functionality of both enzymes. Control and transformed clones are grown in LB with 500 μg/ml of spectinomycin for 24 hours at 37' C. When $OD_{600}$ is measured, 1.247 for the clone with 3' UTR, 0.165 for the clone lacking the 3' UTR, and zero absorbance for the control is observed. As expected the pLD-merAB-3'UTR transformed clone shows a higher growth rate probably caused by the 3' effective termination which allows cells to make more copies of the mer operon transcript that contain only the aadA, merA and merB genes. In chloroplast genome we expect a minor effect in the transcription termination efficiency because the terminator of the genes close to the cassette and downstream can serve as a terminator, once it is integrated in the chloroplast genome by homologous recombination.

Bombardment and regeneration of chloroplast transgenic plants: Tobacco (*Nicotiana tabacum* var. Petit Havana) plants are grown aseptically by germination of seeds on MSO medium (Daniell 1993). Fully expanded, dark green leaves of about two month old plants are bombarded as described by Daniell (1997). The plants are maintained under 500 μg/ml spectinomycin selection in the three phases; first selection (RMOP medium), second round of selection (RMOP medium) and third selection MSO (rooting medium) (FIG. 10). After these selection events, positive transformants are transferred to soil (FIG. 10). The plants are tested for integration of the genes in the chloroplast at first round of selection and before transplanting them to soil. The use of PCR with specific primers that land in the chloroplast genome and in the gene cassette allows us to eliminate mutants and show integration of the selectable marker gene and the mer genes (FIG. 11). After PCR testing, the plants are grown in soil and the seeds are collected.

Polymerase Chain Reaction: PCR is done using DNA isolated from control and transgenic plants to distinguish a) true chloroplast transfomants from mutants and b) chloroplast transformants from nuclear transformants. Primers for testing the presence of the aadA (a gene that confers spectinomycin resistance) in transgenic plants are landed on the aadA coding sequence and 16S rRNA gene (primers 1IP&1M). In order to test chloroplast integration of the mer genes, one primer is landed on the aadA gene while another is landed on the native chloroplast genome (primers 3P&3M). No PCR product is obtained with nuclear transgenic plants using this set of primers. The primer set (5P & 2M) is used to test integration of the entire gene cassette without any internal deletion or looping out during homologous recombination, by landing on the respective recombination sites. This screening is essential to eliminate mutants and nuclear transformants. In order to conduct PCR analyses in transgenic plants, total DNA from unbombarded and transgenic plants are isolated as described by Edwards et al. (1991). Chloroplast transgenic plants containing the mer gene are moved to second round of selection in order to achieve homoplasmy.

Southern Blot Analysis: Southern blots are done to determine the copy number of the introduced foreign gene per cell as well as to test homoplasmy. There are several thousand copies of the chloroplast genome present in each plant cell. Therefore, when foreign genes are inserted into the chloroplast genome, it is possible that some of the chloroplast genomes have foreign genes integrated while others remain as the wild type (heteroplasmy). Therefore, in order to ensure that only the transformed genome exists in cells of transgenic plants (homoplasmy), the selection process is continued. In order to confirm that the wild type genome does not exist at the end of the selection cycle, total DNA from transgenic plants is probed with the chloroplast border (flanking) sequences (the trnI-trnA fragment). If wild type genomes are present (heteroplasmy), the native fragment size will be observed along with transformed genomes. Presence of a large fragment (due to insertion of foreign genes within the flanking sequences) and absence of the native small fragment should confirm homoplasmy (Daniell et al., 1998; Kota et al., 1999; Guda et al., 2000).

The copy number of the integrated gene is determined by establishing homoplasmy for the transgenic chloroplast genome. Tobacco Chloroplasts contain 5000-10,000 copies of their genoine per cell (Daniell et al. 1998). If only a fraction of the genomes are actually transformed, the copy number, by default, must be less than 10,000. By establishing that in the transgenics, the merAB inserted transformed genome is the only one present, one could establish that the copy number is 5000-10,000 per cell. This is done by digesting the total DNA with a suitable restriction enzyme and probing with the flanking sequences that enable homologous recombination into the chloroplast genome. The native fragment present in the control should be absent in the transgenics. The absence of native fragment proves that only the transgenic chloroplast genome is present in the cell and there is no native, untransformed, chloroplast genome, without the mer genes present. This establishes the homoplasmic nature of our transformants, simultaneously providing us with an estimate of 5000-10,000 copies of the foreign genes per cell.

Northern Blot Analysis: Northern blots are done to test the efficiency of transcription of the merAB operon. Total RNA is isolated from 150 mg of frozen leaves by using the "Rneasy Plant Total RNA Isolation Kit" (Qiagen Inc., Chatsworth, Calif.). RNA (10-40 µg) is denatured by formaldehyde treatment, separated on a 1.2% agarose gel in the presence of formaldehyde and transferred to a nitrocellulose membrane (MSI) as described in Sambrook et al. (1989). Probe DNA (merAB gene coding region) is labeled by the random-primed method (Promega) with $^{32}$P-dCTP isotope. The blot is pre-hybridized, hybridized and washed as described above for southern blot analysis. Transcript levels are quantified by the Molecular Analyst Program using the GS-700 Imaging Densitometer (Bio-Rad, Hercules, Calif.).

Plant Bloassays

Germination/Growth Experiments: Seeds of wild-type (Nicotiana tabacum var Petit Havana), transgenic plant pLD-MerAB, and transgenic plant pLD-MerAB-3'UTR are sterilized, vernalized at 4' C for at least 24 h, and germinated on 1% Phytoagar plates (GIBCO/BRL) made with Murashige and Skoog (4.3 g/liter, GIBCO/BRL) medium containing PMA (phenylmercuric acetate) or mercuric chloride. Seedlings are grown at 22° C. with a 16 h light/8 h dark period.

Mercury Vapor Assays: Elemental mercury is relatively insoluble and volatile and lost quickly from cells and media. Volatilized $Hg^0$ is measured on a Jerome 431 mercury vapor analyzer (Arizona Instrument, Phoeniz, Ariz.) (Rugh, C. L. et al., 1996). Approximately 5-10 seedlings (10-14 day old, 10-25 mg total wet weight) are incubated in 2 ml of assay medium (50 mm Tris.HCL, pH 6.8/50 mM NaCl/25 uM $HgCl_2$) in a 16×130 mm test tube with a side arm for gas removal. The Hg $Cl_2$ is added to initiate the assay. The amount of $Hg^0$ produced is assayed by bubbling air through the bottom of the sample for 12 sec at 3 $cm^3$/sec and measuring the release of $Hg^0$. The time zero assay will be taken immediately after the seedlings are placed in the medium. The sample is then reassayed every minute for 10 minutes. The volatilized $Hg^0$ is measured by passing the air sample released from the side arm directly over the gold foil membrane resistor of a Jerome 431 mercury vapor analyzer. The instrument is repeatedly standardized with known quantities of $Hg^0$ (10-200 ng), reduced from $HgCl_2$ with excess $SnCl_2$. The amount of mercury evolved is normalized by dividing the number of nanograms of $Hg^0$ measured by the number of milligrams of seedling tissue in the assay.

Photosynthetic studies: From transgenic plants and untransformed plants, intact chloroplasts are isolated for photosynthetic studies. $O_2$ evolution is studied in an oxygen evolution electrode in the absence or presence of different concentrations of $HgCl_2$ and PMA. Electron transport is studied with suitable electron donors/acceptors to study photosystem I, II or both. PAGE is used to examine the composition of PSII complex, especially EP33, after incubation of cells or chloroplasts or thylakoid membranes with different concentrations of $HgCl_2$ and PMA. In vivo chloroplast fluorescence is studied to monitor changes in control and transformed cells or chloroplasts to measure Fo, Fm, Fv.

Inheritance of Introduced Foreign Genes: While it is unlikely that introduced DNA would move from the chloroplast genome to nuclear genome, it is possible that the gene could get integrated in the nuclear genome during bombardment and remain undetected in Southern analysis. Therefore, in initial tobacco transformants, some are allowed to self-pollinate, whereas others are used in reciprocal crosses with control tobacco (transgenics as female accepters and pollen donors; testing for maternal inheritance). Harvested seeds (TI) are germinated on media containing spectinomycin. Achievement of homoplasmy and mode of inheritance is classified by looking at germination results. Homoplasmy is indicated by totally green seedlings (Daniell et al., 1998) while heteroplasmy is displayed by variegated leaves (lack of pigmentation, Svab & -Maliga, 1993). Lack of variation in chlorophyll pigmentation among progeny also underscores the absence of position effect, an artifact of nuclear transformation. Maternal inheritance is demonstrated by sole transmission of introduced genes via seed generated on transgenic plants, regardless of pollen source (green seedlings on selective media). When transgenic pollen is used for pollination of control plants, resultant progeny would not contain resistance to chemical in selective media (will appear bleached; Svab and Maliga, 1993). Molecular analyses confirms transmission and expression of introduced genes, and T2 seed are generated from those confirmed plants by the analyses described above.

EXAMPLE 3

Chlorella vulgaris transformation vector: The region 16S to 23S of the Chlorella vulgaris chloroplast genome is amplified by PCR using specific primers complementary to rrn16 and to rrn23. The PCR product will be cloned into pCR 2.1 vector available from Promega. The PCR product 16S to 23S is removed from the pCR2.1 vector by a blunt end restriction endonuclease and cloned into the pUC 19 in which the multiple cloning site has been removed using a blunt end restriction enzyme (PvuII). Then the cassette containing the promoter, the antibiotic resistance gene and the merAB genes is inserted into the new vector (*Chlorella* transformation vector) using a blunt end restriction enzyme (HincII) that is present in the spacer region between trnA and trnT. The final construct is used for the transformation of *Chlorella vulgaris* (FIG. 12).

Bombardment and transformation of *Chlorella vulgaris*: The biolistic transformation method (Sanford et al. 1993) is optimized for transformation of *Chlorella vulgaris*. *Chlorella* is grown in liquid heterotrophic medium (5 sporulation agar) at 25° C. to late-log phase (~6×10$^6$ cells/ml). To prepare a monolayer for bombardment (2×10$^7$), cells are collected onto prewetted 45 mm GVWP filters (Millipore) under gentle (30 mBar) vacuum. Gold particles are coated with the transforming plasmid. (Sanford et al. 1993) The monolayer filters are bombarded. Immediately after bombardment, filters are transferred to selective solid media containing 500 µg/ml spectinomycin and incubated at 22° C. under high light. After approximately 6 weeks, green colonies are picked from a background of bleached cells onto selective plates and grown for an additional 1-2 weeks. Colonies are harvested and screened for integration of foreign genes when they reached a diameter of approximately 5 mm.

*Chlorella vulgaris* Bioassays: Growth and colonies formation bioassay are performed as explained in the plant germination growth experiment; the only change is the use of *Chlorella* specific media.

Mercury vapor assays: Mercury vapor assays are performed in the way explained for plants above except changing the growth media specific to *Chlorella*, including temperature and light intensity.

Photosynthetic studies: Photosynthetic studies are performed in the way explained for plants above except untransformed and transformed *Chlorella* cells will be directly used to study the effect of mercury toxicity.

EXAMPLE 4

*Synechocystis* transformation vector: The region 16S to 23S of the *Synechocystis* genome is amplified by PCR using specific primers complementary to rrn116 and to rrn23. The PCR product is cloned into the pCR 2.1 vector available from Promega. The PCR product 16S to 23S is removed from the pCR2.1 vector by a blunt end restriction endonuclease and cloned into pUC19 in which the multiple cloning site has been removed using a blunt end restriction enzyme (PvuII). Then the cassette containing the promoter, the antibiotic resistance gene and the merAB genes is inserted into the new vector (*Synechocystis* transformation vector) using a blunt end restriction enzyme (HincII) that is present in the spacer region between trnI and trnA. The final construct will be used for the transformation of *Synechocystis* (FIG. 13).

Transformation of *Synechocystis*: A fresh culture of wild type in BG-11 (heterotrophic medium) plus glucose is grown to OD$_{730}$=0.5 after 2-3 days of culture. Cells are spun down in sterile 50 ml tubes at room temperature and resuspended in the original growth medium to OD$_{730}$=2.5. Transforming DNA is added to resuspended cells in sterile glass culture tubes. Tubes are placed in rack in the growth chamber at 30° C. for 6 hours and shaken for 3 hours. Cells (200 µl) are plated on a sterile filter that has been placed on a BG-11 plus glucose plate and spread around. After growth for 24 hours and they are transferred to filters on appropriate medium containing spectinomycin or mercuric chloride.

*Synechocystis* Bioassays: Growth and colonies formation bioassay are performed as explained in the plant germination-growth experiment; the only change is the use *Synechocystis* growth media.

Mercury vapor assays: Mercury vapor assays are performed in the way explained for plants above except changing the growth media specific to the *Synechocystis*, including temperature and light intensity.

Photosynthetic studies: Photosynthetic studies are performed in the way explained for plants above except untransformed and transformed *Synechocystis* cells are directly used to study the effect of mercury toxicity.

EXAMPLE 5

Lemna transformation vector: The Lemna chloroplast vector, as shown in FIG. 14, is constructed in the same way as explained above for tobacco, with the exception that the Lemna chloroplast DNA flanking sequences are used.

Bombardment and regeneration of transgenic plants: Lemna plants are transformed and regenerated in the way explained for tobacco in Example 1 above.

Plant Bioassays: Various plant bioassays are performed as explained for tobacco in Example 1 above.

EXAMPLE 6

Sugarcane transformation vector: The Sugarcane chloroplast vector, as shown in FIG. 15, is constructed in the same way as explained above for tobacco, with the exception that the Sugarcane chloroplast DNA flanking sequences are used.

Bombardment and regeneration of transgenic plants: Sugarcane plants are transformed and regenerated in the way explained for tobacco in Example 1 above.

Plant Bioassays: Various plant bioassays are performed as explained for tobacco in Example 1 above.

REFERENCES

Begley T P A, Walts A E, Walsh C T (1986) Mechanistic studies of a protonolytic organomercurial cleaving enzyme: bacterial organomercurial lyase. Biochemistry 25: 7192-7200.

Bernier M, Popovic R, Carpentier R (1993) Mercury inhibition of photosystem 11. FEBS Lett. 32: 19-23.

Bernier M, Carpentier R (1995) The action of mercury on the binding of extrinsic polypeptides associated with water oxidizing complex of photosystem. II.

Bizily S, Rugh C C, Summers A O, Meagher R B (1999) Phytoremediation of methylmercury pollution: merB expression in *Arabidopsis thaliana* plants confer resistance to organomercurial. PNAS 96: 6808-6813.

Bizily S, Rugh C C, Meagher R B (2000) Phytoremediation of hazardous organomercurials by genetically engineered plants. Nature Biotechnology 18; 213-217.

Bogorad, L. Engineering chloroplasts: an alternative site for foreign genes, proteins, reactions, and products. Trends in Biotechnology. 18, 257-263 (2000).

Bradley, D. et al. The insecticidal CrylB crystal protein of *Bacillus thuringiensis* ssp. *Thuringiensis* has dual specificity to coleopteran and lepidopteran larvae. J. Invert. Pathol. 65, 162-173 (1995).

Carlson P S (1973) The use of protoplasts for genetic research. Proc. Natl. Acad. Sci. USA70: 598-602.

Compeau G C, Bartha R (1985) Sulfate-reducing bacteria: principal methylators in freshwater sediments. Appl. Environ. Microbiol, 50: 498-502.

Crickmore, N. & Ellar, D. Involvement of a possible chaperonin in the efficient expression of a cloned cryIIA 8-enclotoxin gene in *Bacillus thuringiensis*. Mol. Microbiol. 6, 1533-1537 (1992).

Crickmore, N., Wheeler, V. & Ellar, D. Use of an operon fusion to induce expression and crystallisation of a *Bacillus thuringiensis* 5-endotoxin encoded by a cryptic gene. MoL Gen. Genet. 242, 365-368 (1994).

Daniell, H. Foreign gene expression in chloroplasts of higher plants mediated by tungsten particle bombardment. Methods Enzymo/. 217, 536-556 (1993).

Daniell, H. et al. Engineering plants for stress tolerance via organelle genomes. NATO ASI Series. 86, 589-592 (1994).

Daniell, H. Transformation and foreign gene expression in plants mediated by microprojectile bombardment. Meth. Mol. Biol. 62, 463-489 (1997).

1 A operons on the formation of Cry2A inclusions in *Bacillus thuringiensis*. FEMS Microbiol. Lett. 165, 35-41 (1998).

Daniell, H. et al. Containment of a herbicide resistance through genetic engineering of the chloroplast genome. Nature Biotechnol. 16, 345-348 (1998).

Daniell, H. GM crops: public perception and scientific solutions. Trends in Plant Science. 4, 467-469 (1999).

Daniell, H. New tools for chloroplast genetic engineering. Nat. Biotechno'll. 17, 855-856 (1999).

Daniell H, Kulandaivelu G and Chandrasingh U (1980) Substituted p-benzoquinones having high electron affinity as photosystem II electron acceptors. Z. Naturforsch. 35C, 136-138.

Daniell H and Sarojini G (1981) Site of action of 2,5-dimethoxy-3,6-dichloro-p-benzoqliinone in the photosynthetic electron transport chain. Z. Naturforsch. 36C, 656-661.

Daniell H, Ramanujan P, Krishnan M, Gnanam A, Rebeiz C A (1983) In vitro synthesis of photosynthetic membranes: I. Development of photosystem I activity and cyclic phosphorylation. Biochem. Biophys. Res. Comun. 11 1: 740-749.

Daniell H, Krishnan M, Renganathan M and Gnanam A (1984) Radioisotopic evidence for the polypeptides associated with photosystem II activity. Biochem. Biophys. Res. Commun. 125, 988-995.

Daniell H, Anbudurai P R, Periyanan S, Renganathan M, Bhardwaj R, Kulandaivelu G and Gnanam A (1985) Oxygenic photoreduction of methyl viologen without the involvement of photosystem I during plastid development. Biochem. Biophys. Res. Commun. 126, 1114-1121.

Daniell H and McFadden B A (1986) Characterization of DNA uptake by the cyanobacterium *Anacystis nidulans*. Mol. Gen. Genetics 204, 243-248.

Daniell H, Sarojini G and McFadden B A (1986) Transformation of the cyanobacterium *Anacystis nidulans* 6301 with the *Escherichia coli* plasmid pBR322. Proc. Natl. Acad. Sci. USA 83, 2546-2550.

Daniell H and McFadden B A (1987) Uptake and expression of bacterial and cyanobacterial genes by isolated cucumber etioplasts. Proc. Natl. Acad. Sci. USA 84: 6349-6353.

Daniell H and McFadden B A (1988) Genetic Engineering of plant chloroplasts. U.S. Pat. Nos. 5,932,479; 5,693,507.

Daniell H, Vivekananda J, Neilsen B, Ye G N, Tewari K K, Sanford J C (1990) Transient foreign gene expression in chloroplasts of cultured tobacco cells following biolistic delivery of chloroplast vectors. Proc. Natl. Acad. Sci. USA 87: 88-92.

Daniell H, Krishnan M, McFadden B A (1991) Expression of B-glucuronidase gene in different cellular compartments following biolistic delivery of foreign DNA into wheat leaves and calli. Plant Cell Reports 9: 615-619.

Daniell H, Muthukumar B and Lee S B (2001) Marcer free transgenic plants: engineering the chloroplast genome without the use of antibiotic selection. Current Genetics. In press.

DeCosa B, Moar W, Lee S B, Miller M, Daniell H (2001). Hyper-expression of the Bt Cry2Aa2 operon in chloroplasts leads to formation of insecticidal crystals. Nature Biotechnol. 19: 71-74.

De Wilte, C. et. al. (2000). Plants as Bioreacters for Protein Production: Avoiding the Problem of Transgene Silencing. Plant Molecular Biology 43:347-389.

Edwards K, Johnstone C, Thompson C (1991) A simple and rapid method for preparation of plant genomic DNA for PCR analysis. Nucleic Acids Res. 19: 1349.

Foster T J (1983) Plasmid-determined resistance to antimicrobial drugs and toxic metal ions in bacteria. Microbiol. Rev. 47: 361-409.

Ge, B. et al. Differential effects of helper proteins encoded by the cry2A and cry1 Greenplate, J. Quantification of *Bacillus thuringiensis* insect control protein Cry1Ac over time in bollgard cotton fruit and terminals. J. Econ.Entomo/. 92, 1377-1383 (1999).

Gilmour C C, Henry E A, Mitchel R (1992) Sulfate stimulation of mercury methylation in freshwater sediments. Environ. Sci. Technol. 26: 2281-2287.

Guda, C., Lee, S. B. & Daniell, H. Stable expression of a biodegradable protein-based polymer in tobacco chloroplasts. Plant Cell Reports. 19, 257-262 (2000).

Harada M, Minamata Disease Research Group (1995) Minamata disease: methylmercury poisoning in Japan caused by environmental pollution. Crit. Rev. Toxicol. 25: 1-24.

Kota, et al. Overexpression of the *Bacillus thuriniensis* (13t) Cry2Aa? protein 9 in chloroplasts confers resistance to plants against susceptible and Bt-resistant insects. Proc. Nati. Acad. Sci. 96,1840-1845 (1999).

Kulandaivelu G and Daniell H. (1980) Dichlorophenyl dimethylurea (DCMU) induced increase in chlorophyll a fluorescence intensity: An index of photosynthetic oxygen evolution in leaves, chloroplasts and algae. Physiol. Plant. 48, 385-388.

Ma, J. et al. Generation and assembly of secretary antibodies in plants. Science. 268, 716-719 (1995).

McBride K E, Svab Z, Schaaf D J, Hogen P S, Stalker D M, Maliga P (1995) Amplification of a chimeric *Bacillus* gene in chloroplasts leads to extraordinary level of an insecticidal protein in tobacco. Bio/technology 13: 362-365.

Minamata Disiase Research Group (1968) Minamata Disease. (Medical School of Kumamoto University, Kumamoto, Japan)

Moar, W. et al. Insecticidal activity of the Cry11A protein from the NRD-12 isolate of *Bacillus thuringiensis* subsp. kurstaki expressed in *Escherichia coli* and *Bacillus thuringiensis* and in a leaf-colonizing strain of *Bacillus cereus*. Appl. Environ. Microbiol. 60, 896-902 (1994).

Moar, W. et al. Development of *Bacillus thuringiensis* Cryl C resistance by *Spodoptera exigua*. Appl. Environ. Microbiol. 61, 2086-2092 (1995).

Navrath, C., Poirier, Y., & Somerville, C. Targeting of the polyhydroxybutyrate biosynthetic pathway to the plastis of *Arabidopsis thaliana* results in high levels of polymer accumulation. Proc. Natl. Acad. Sci. 91, 12760-12764 (1994).

Peerenboom, E (2000) German health minister calls time out for Bt maize. Nature Biotechnol. 18: 374.

Puchta H (2000) Removing selectable marker genes: taking the shortcut. Trends in plant Science 5: 273-274.

Rashid A, Popovic R (1990) Protective role of $CaCl_2$ against $Pb^{2+}$ inhibition in photosystem II. FEBS Lett. 271: 181-184.

Roy, H. & Nierzwicki-Bauer, S. RuBisCo: genes, structure, assembly and evolution. The Photosynthetic Apparatus, L. Bogorad, 1. Vasil (eds), pp 347-364, Academic Press, NY. (1994).

Rugh C C, Summers A O, Meagher R B (1996) Mercuric ion reductase and resistance in transgenic *Arabidopsis thaliana* plants expressing modified bacterial merA gene. PNAS 93: 3182-3187.

Salt D E et al. (1998) Phytoremediation. Rev. Plant. Physiol. Plant. Mol. Biol. 49: 643-668.

Sanford J C, Smith F D, Russell J A (1993) Optimizing the biolistic process for different biological applications. Methods Enzymol. 217: 483-509.

Sambrook J, Fritch E F, Maniatis T (1989) Molecular cloning. Cold Spring Harbor Press, Cold Spring Harbor, N.Y.

Sarojini G, Daniell H and Vermaas W F J (1981) Site of electron acceptance by 3,6,dichloro-2,5-dimethoxy-p-benzoquinone and its relation to the bicarbonate effect on photosynthetic electron transport Biochem. Biophys. Res. Commun. 102, 944-951.

Sidorov V A, Kasten D, Pang S Z, Hajdukiewicz P T J, Staub J M, Nehra N S (1999) Stable chloroplast transformation in potato: use of green fluorescent protein as a plastid marker. Plant Journal 19: 209-216.

Staub J M, Garcia B, Graves J, Hajdukiewicz P T J, Hunter P, Nehra N, Paradkar V, Schlittler M, Caroll J A, Spatola L, Ward D, Ye G, Russell D (2000) High-yield production of human therapeutic protein in tobacco chloroplast. Nature Biotechnol. 18: 333-338.

Summers A O, Silver S (1978) Microbial transformation of metals. Annu. Rev. Microbiol. 32: 637-672.

Summers A O (1986) Organization, expression, and evolution of genes for mercury resistance. Annu. Rev. Microbiol. 40: 607-634.

Svab Z, Maliga P (1993) High frequency plastid transformation in tobacco by selection for a chimeric aadA gene. Proc. Natl. Acad. Sci. USA 90: 913-917.

Trebs A (1980) Inhibitors in electron flow: tools for the functional and structural localization of carriers and energy conservation sites.

A. J Vrekleij, J. M. Leunissen (eds.), Immuno-gold Labeling in Cell Biology CRC Press, Boca Raton, Fla. (1989).

Yamamoto, T. & Iizuka, T. Two types of entomocidal toxins in the parasporal crystals of *Bacillus thuringiensis* var. kurstaki. Archives Biochem. Biophys. 227, 233241 (1983).

Ye, X. et al, Engineering the provitamin A (0-carotene) biosynthetic pathway into (carotenoid-free) rice enclosperm. Science. 287, 303-305 (2000).

Herbicide Resistance Crops, Agricultural, Environmental, Economic, Regulatory and Technical Aspects, Duke, S. O., edt., CRC Press, Inc. (1996).

Herbicide Resistance in Plants, Biology and Biochemistry, Powles, S. B., and Holturn, J. A. M., eds., CRC Press, Inc. (1994).

Peptides: Design, Synthesis, and Biological Activity, Basava, C. and Anantharamaiah, G. M., eds., Birkhauser Boston, 1994.

Protein Folding: Deciphering the Second Half of the Genetic Code, Gierasch, L. M., and King, J., eds., American Association For the Advancement of Science (1990).

The invention claimed is:

1. A tobacco chloroplast transformation and expression vector which is capable of introducing multiple genes in a multi-gene operon into a selected tobacco plant by a single integration event, said vector comprising as operably linked components,
 a first flanking sequence complementary to a first sequence of a tobacco chloroplast genome,
 a tobacco chloroplast promoter operably linked to a multi-gene operon,
 a transcription termination region functional in a tobacco chloroplast, and
 a second flanking sequence complementary to a second sequence of said tobacco chloroplast genome,
 said multi-gone operon comprising a first open reading frame encoding a first protein and a second open reading frame encoding a second protein,
 wherein transcription of said multi-gene operon generates a polycistron encoding said fast protein and said second protein,
 wherein one of said proteins is a biopharmaceutical protein selected from the group consisting of insulin or human serum albumin, and
 wherein one of said proteins is a chaperonin,
 whereby integration of the vector into said chloroplast genome comprising said first sequence and said second sequence is facilitated through homologous recombination of the flanking sequences and the chloroplast genome sequences.

2. A tobacco chloroplast transformation and expression vector which is capable of introducing multiple genes in a multi-gene operon into a selected tobacco plant by a single integration event, said vector comprising as operably linked components,
 a first flanking sequence complementary to a first sequence of a tobacco chloroplast genome,
 a tobacco chloroplast promoter operably linked to a multi-gene operon, a transcription termination region functional in a tobacco chloroplast, and a second flanking sequence complementary to a second sequence of said tobacco chloroplast genome, said multi-gene operon comprising a first open reading frame encoding a first protein, a second open reading frame encoding a second protein, and a third open reading frame encoding a third protein, wherein transcription of said multi-gene operon generates a polycistron encoding said first protein, said second protein, and said third protein, and wherein one protein is a biopharmaceutical protein, one protein is a chaperonin, and one protein is a selectable marker, whereby integration of the vector into said chloroplast genome comprising said first sequence and said second sequence is facilitated through homologous recombination of the flanking sequences and the chloroplast genome sequences.

* * * * *

UNITED STATES PATENT AND TRADEMARK OFFICE
CERTIFICATE OF CORRECTION

PATENT NO. : 7,294,506 B2
APPLICATION NO. : 10/770183
DATED : November 13, 2007
INVENTOR(S) : Henry Daniell and William Moar It is certified that error appears in the above-identified patent and that said Letters Patent is hereby corrected as shown below:

Column 1,
Line 50, "method of 26 genetically" should read --method of genetically--.

Column 5,
Line 60, "attp" should read --atpβ--.

Column 6,
Line 27, "6-endotoxin" should read --δ-endotoxin--.

Column 8,
Line 57, "shows analysis" should read --shows PCR analysis--.
Line 60, "cry2Aa2" should read --Cry2Aa2--.
Line 61, "cry2Aa2" should read --Cry2Aa2--.

Column 9,
Line 29, "cry2Aa2" should read --Cry2Aa2--.
Line 33, "cry2Aa2" should read --Cry2Aa2--.
Line 42, "cry2Aa2" should read --Cry2Aa2--.

Column 10,
Line 31, "of heterologous" should read --of a heterogolous--.

Column 15,
Line 42, "aada" should read --aadA--.

Column 16,
Line 55, "To plant" should read --$T_0$ plant--.

Column 21,
Line 12, "liquant" should read --μ Quant--.

Column 28,
Line 5, "Marcer" should read --Marker--.

UNITED STATES PATENT AND TRADEMARK OFFICE
CERTIFICATE OF CORRECTION

PATENT NO. : 7,294,506 B2 Page 2 of 2
APPLICATION NO. : 10/770183
DATED : November 13, 2007
INVENTOR(S) : Henry Daniell and William Moar It is certified that error appears in the above-identified patent and that said Letters Patent is hereby corrected as shown below:

<u>Column 31,</u>
Line 66, "fast" should read --first--.

Signed and Sealed this

Fifth Day of August, 2008

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
acaatgtagc cgtactggaa ggtgcgggtg                                            30

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 2
cgcgcttagc tggataacgc cacggaa                                               27

<210> SEQ ID NO 3
<211> LENGTH: 25
<212> TYPE: DNA
```

```
<213> ORGANISM: Artificial Sequence
<220> FEATURE:
<223> OTHER INFORMATION: Description of Artificial Sequence: Primer

<400> SEQUENCE: 3
aaaacccgtc ctcagttcgg attgc                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
ccgcgttgtt tcatcaagcc ttacg                                          25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
ctgtagaagt caccattgtt gtgc                                           24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
tgactgccca acctgagagc ggaca                                          25
```